US012618046B2

(12) United States Patent
Veltmeyer

(10) Patent No.: US 12,618,046 B2
(45) Date of Patent: May 5, 2026

(54) GENERATION OF TUMOR IMMUNITY USING ASTROCYTES AND ASTROCYTE-DENDRITIC CELL COMBINATIONS

(71) Applicant: James Veltmeyer, La Jolla, CA (US)

(72) Inventor: James Veltmeyer, La Jolla, CA (US)

( * ) Notice: Subject to any disclaimer, the term of this patent is extended or adjusted under 35 U.S.C. 154(b) by 506 days.

(21) Appl. No.: 18/191,791

(22) Filed: Mar. 28, 2023

(65) Prior Publication Data

US 2023/0303973 A1    Sep. 28, 2023

Related U.S. Application Data

(60) Provisional application No. 63/324,593, filed on Mar. 28, 2022.

(51) Int. Cl.
*C12N 5/079* (2010.01)
*A61P 35/00* (2006.01)

(52) U.S. Cl.
CPC ............ *C12N 5/0622* (2013.01); *A61P 35/00* (2018.01); *C12N 2502/1121* (2013.01); *C12N 2502/30* (2013.01)

(58) Field of Classification Search
CPC .......... A61P 35/00–04; C12N 2502/30; C12N 2502/086; C12N 5/0622; C12N 5/0639; C12N 2502/1121
See application file for complete search history.

(56) References Cited

PUBLICATIONS

Liau et al. "Treatment of intracranial gliomas with bone marrow-derived dendritic cells pulsed with tumor antigens" J Neurosurg 90: 1115-1124, 1999 (Year: 1999).*
Söling et al. "Dendritic Cell Therapy of Primary Brain Tumors" Molecular Medicine 7(10): 659-667, 2001 (Year: 2001).*
Zhang et al. "Nanotherapeutic Modulation of Human Neural Cells and Glioblastoma in Organoids and Monocultures" Cells 2020, 9, 2434; 17 pages (Year: 2020).*

* cited by examiner

*Primary Examiner* — Thane Underdahl
(74) *Attorney, Agent, or Firm* — Baumgartner Patent Law LLC; Marc Baumgartner

(57) ABSTRACT
Disclosed are means, methods, and compositions of matter useful for treatment of oncological indications through stimulation of protective anti-cancer immunity. In one embodiment the invention discloses the unexpected effect of astrocytes to augment immune stimulating activities of dendritic cells. In one embodiment dendritic cells are pulsed with tumor lysates and subsequently co-cultured with astrocytes in the presence of toll-like receptor agonists.

13 Claims, 8 Drawing Sheets

GENERATION OF TUMOR IMMUNITY USING ASTROCYTES AND ASTROCYTE-DENDRITIC CELL COMBINATIONS

CROSS-REFERENCE TO RELATED APPLICATIONS

This application claims priority to U.S. Provisional Application No. 63/324,593, titled "Generation of Tumor Immunity Using Astrocytes and Astrocyte-Dendritic Cell Combinations" filed Mar. 28, 2022, which is hereby incorporated by reference herein in its entirety.

FIELD OF THE INVENTION

The invention relates to cancer treatments using astrocytes and astrocyte-like cells for immune modulation.

BACKGROUND OF THE INVENTION

There is currently a great desire to induce immunologically mediated treatments of chronic diseases. Immunotherapy, such as immune checkpoint inhibitors, include antibodies that block negative regulators of T-cell activation. These approaches have radically transformed cancer treatment (Eggermont et al., 2018; Gandhi et al., 2018; Schachter et al., 2017). However, even in metastatic melanoma and non-small cell lung cancer (NSCLC), malignancies that are highly responsive to immune checkpoint inhibitor therapy, response rates rarely exceed 40%.

Furthermore, many common malignances, including prostate cancer (PCa) and pancreatic ductal adenocarcinoma (PDAC), are refractory to immune checkpoint inhibitors but causes of treatment failure are largely unknown. Early work correlated responsiveness with mutational burden, which presumably drives production of neoantigens that are recognized by CTL. Although this correlation may hold for a single tumor type, several malignances initially predicted to be nonresponsive based on low mutational burdens, e.g., renal cell carcinoma (RCC) and hepatocellular carcinoma (HCC), were found to be nearly as responsive to PD-1 inhibitors as highly mutated NSCLC.

There is a need to induce immunotherapeutic responses in patients who are refractory to current immune stimulatory approaches due to limited ability to induce sufficient dendritic cell activation to overcome tolerogenic processes. The current invention provides means of augmenting DC activation and lymphoid in terms of proliferation, cytotoxic activity and immune stimulatory activity.

SUMMARY OF THE INVENTION

Preferred embodiments are directed to methods of treating cancer comprising the steps of: a) obtaining a population of astrocyte or astrocyte-like cells; b) contacting said population of astrocyte or astrocyte-like cells with a population of dendritic cells; c) introducing one or more tumor antigens into said culture of astrocyte and/or astrocyte-like cells with dendritic cells; d) inducing maturation of said dendritic cells and e) administering said activated dendritic cells into a mammal in need of treatment.

Preferred methods include embodiments wherein said astrocyte-like cells are derived from mammalian astrocyte restricted precursor cells being CD44 immunoreactive and generating astrocytes but not oligodendrocytes.

Preferred methods include embodiments wherein said astrocyte progenitors express CD105.

Preferred methods include embodiments wherein said astrocyte progenitors express CD123.

Preferred methods include embodiments wherein said astrocyte progenitors express IL-3 receptor.

Preferred methods include embodiments wherein said astrocyte progenitors express c-met.

Preferred methods include embodiments wherein said astrocyte progenitors express Nanog.

Preferred methods include embodiments wherein said astrocyte progenitors express Sox-2.

Preferred methods include embodiments wherein said astrocyte progenitors express aldehyde dehydrogenase family 1 member L1 (Aldh1L1).

Preferred methods include embodiments wherein said astrocyte progenitors express aldolase C (AldoC).

Preferred methods include embodiments wherein said astrocyte progenitors glutamate transporter-1 (Glt1).

Preferred methods include embodiments wherein said astrocyte progenitors express S100 calcium-binding protein B (S100b).

Preferred methods include embodiments wherein said astrocyte progenitors express Aquaporin 4.

DETAILED DESCRIPTION OF THE INVENTION

Figure 1:
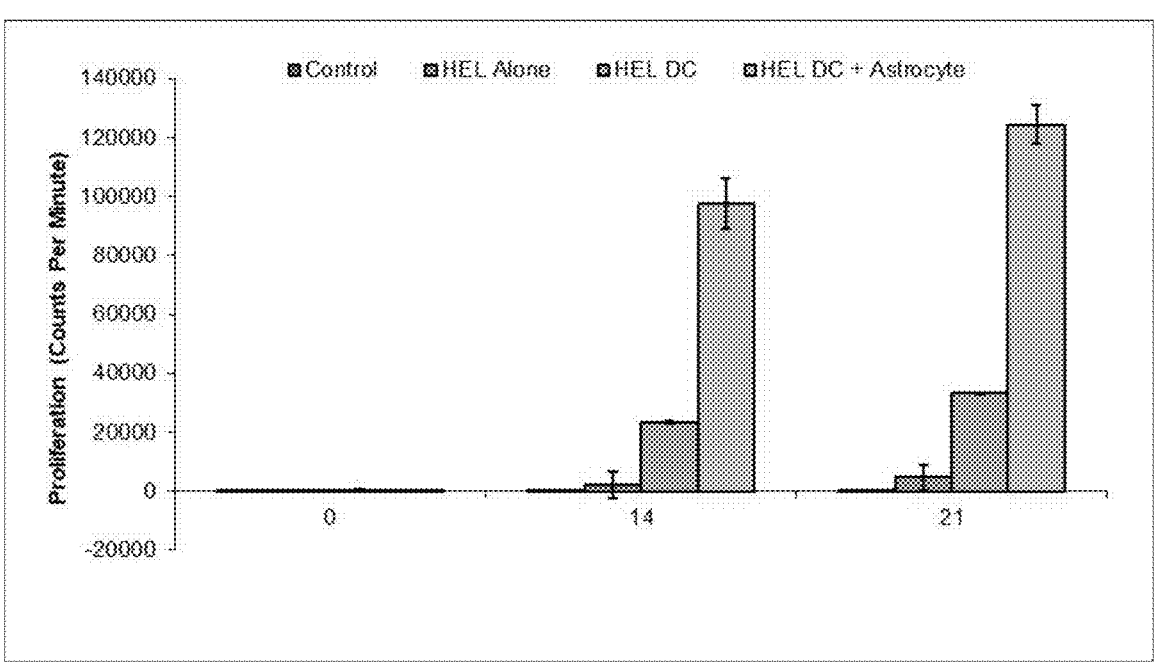
FIG. 1 is a bar graph showing the proliferation of HEL alone, HEL DC, and HEL DC and Astrocytes

The invention provides means of enhancing the immune activation ability of dendritic cells using coculture techniques with astrocytes and/or astrocyte progenitors. Through enhancing ability of dendritic cells to induce T cell and/or NK cell activation, the invention provides means of treatment for conditions that benefit from immune activation. In one embodiment the invention provides means of enhancing therapeutic efficacy of immunotherapy that can be either prophylactic, as in vaccines, or therapeutic as in immune activatory treatments.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

The term "subject" as used herein refers to any individual or patient to which the subject methods are performed. Generally, the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

A subject "in need" of treatment with the invention's methods includes a subject that is "suffering from disease," i.e., a subject that is experiencing and/or exhibiting one or more symptoms of the disease, and a subject "at risk" of the disease. A subject "in need" of treatment includes animal models of the disease. A subject "at risk" of disease refers to a subject that is not currently exhibiting disease symptoms and is predisposed to expressing one or more symptoms of the disease. This predisposition may be genetic based on family history, genetic factors, environmental factors such as exposure to detrimental compounds present in the environment, etc.). It is not intended that the present invention be limited to any particular signs or symptoms. Thus, it is intended that the present invention encompass subjects that are experiencing any range of disease, from sub-clinical symptoms to full-blown disease, wherein the subject exhibits at least one of the indicia (e.g., signs and symptoms) associated with the disease.

The term "administering" to a subject means delivering a molecule, drug, or composition to a subject. "Administering" a composition to a subject in need of reducing a disease and/or of reducing one or more disease symptoms includes prophylactic administration of the composition (i.e., before the disease and/or one or more symptoms of the disease are detectable) and/or therapeutic administration of the composition (i.e., after the disease and/or one or more symptoms of the disease are detectable). When the methods described herein include administering a combination of a first composition and a second composition, the first and second compositions may be administered simultaneously at substantially the same time, and/or administered sequentially at different times in any order (first composition followed second composition, or second composition followed by first composition). For example, administering the second composition substantially simultaneously and sequentially in any order includes, for example, (a) administering the first and second compositions simultaneously at substantially the same time, followed by administering the first composition then the second composition at different times, (b) administering the first and second compositions simultaneously at substantially the same time, followed by administering the second composition then the first composition at different times, (c) administering the first composition then the second composition at different times, followed by administering the first and second compositions simultaneously at substantially the same time, and (d) administering the second composition then the first composition at different times, followed by administering the first and second compositions simultaneously at substantially the same time.

As used herein, an "effective amount" is an amount of a substance or molecule sufficient to effect beneficial or desired clinical results including alleviation or reduction in any one or more of the symptoms associated with cancer. For purposes of this invention, an effective amount of a compound or molecule of the invention is an amount sufficient to reduce the signs and symptoms associated with cancer and/or to induce expression of one or more genes associated with cell surface antigens.

The terms "reduce," "inhibit," "diminish," "suppress," "decrease," and grammatical equivalents when used in reference to the level of any molecule (e.g., amino acid sequence, and nucleic acid sequence, antibody, etc.), cell (e.g., B cell, T cell, tumor cell), and/or phenomenon (e.g., disease symptom), in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis.

The terms "increase," "elevate," "raise," and grammatical equivalents (including "higher," "greater," etc.) when used in reference to the level of any molecule (e.g., amino acid sequence, and nucleic acid sequence, antibody, etc.), cell (e.g., B cell, T cell, tumor cell), and/or phenomenon (e.g., disease symptom), in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis.

As used herein, "treatment" is an approach for obtaining beneficial or desired clinical results. For purposes of this invention, beneficial or desired clinical results include, but are not limited to, treatment of cancer, such as non-small cell lung cancer (NSCLC), prostate cancer (PCa), pancreatic ductal adenocarcinoma (PDAC), renal cell carcinoma (RCC) and hepatocellular carcinoma (HCC).

As used herein, the term "cancer cell" refers to a cell undergoing early, intermediate or advanced stages of multi-step neoplastic progression as previously). This includes cells in early, intermediate and advanced stages of neoplastic progression including "pre-neoplastic" cells (i.e., "hyperplastic" cells and dysplastic cells), and neoplastic cells in advanced stages of neoplastic progression of a dysplastic cell.

As used herein, a "metastatic" cancer cell refers to a cancer cell that is translocated from a primary cancer site (i.e., a location where the cancer cell initially formed from a normal, hyperplastic or dysplastic cell) to a site other than the primary site, where the translocated cancer cell lodges and proliferates.

As used herein, the term "cancer" refers to a plurality of cancer cells that may or may not be metastatic, such as prostate cancer, liver cancer, bladder cancer, skin cancer (e.g., cutaneous, melanoma, basal cell carcinoma, Kaposi's sarcoma, etc.), ovarian cancer, breast cancer, lung cancer, cervical cancer, pancreatic cancer, colon cancer, stomach cancer, esophagus cancer, mouth cancer, tongue cancer, gum cancer, muscle cancer, heart cancer, bronchial cancer, testis cancer, kidney cancer, endometrium cancer, and uterus cancer. Cancer may be a primary cancer, recurrent cancer, and/or metastatic cancer. The place where a cancer starts in the body is called the "primary cancer" or "primary site." If cancer cells spread to another part of the body the new area of cancer is called a "secondary cancer" or a "metastasis." "Recurrent cancer" means the presence of cancer after treatment and after a period of time during which the cancer cannot be detected. The same cancer may be detected at the primary site or somewhere else in the body, e.g., as a metastasis.

As used herein, the term "genetic modification" is used to refer to any manipulation of an organism's genetic material in a way that does not occur under natural conditions. Methods of performing such manipulations are known to those of ordinary skill in the art and include, but are not limited to, techniques that make use of vectors for transforming cells with a nucleic acid sequence of interest. Included in the definition are various forms of gene editing in which DNA is inserted, deleted or replaced in the genome of a living organism using engineered nucleases, or "molecular scissors." These nucleases create site-specific double-strand breaks (DSBs) at desired locations in the genome. The induced double-strand breaks are repaired through nonhomologous end-joining (NHEJ) or homologous recombination (HR), resulting in targeted mutations (i.e., edits). There are several families of engineered nucleases used in gene editing, for example, but not limited to, meganucleases, zinc finger nucleases (ZFNs), transcription activator-like effector-based nucleases (TALEN), and the CRISPR-Cas system.

A "test agent" or "candidate agent" refers to an agent that is to be screened in one or more of the assays described herein. The agent can be virtually any chemical compound. It can exist as a single isolated compound or can be a member of a chemical (e.g., combinatorial) library. In one embodiment, the test agent is a small organic molecule. The term small organic molecule refers to molecules of a size comparable to those organic molecules generally used in pharmaceuticals. The term excludes biological macromolecules (e.g., proteins, nucleic acids, etc.). In certain embodiments, small organic molecules range in size up to about 5000 Da, up to 2000 Da, or up to about 1000 Da.

As used herein, the terms "sample" and "biological sample" refer to any sample suitable for the methods provided by the present invention. In one embodiment, the biological sample of the present invention is a tissue sample, e.g., a biopsy specimen such as samples from needle biopsy (i.e., biopsy sample). In other embodiments, the biological sample of the present invention is a sample of bodily fluid, e.g., serum, plasma, sputum, lung aspirate, urine, and ejaculate.

The term "antibody" is meant to include intact molecules of polyclonal or monoclonal antibodies, chimeric, single chain, and humanized antibodies, as well as fragments thereof, such as Fab and F(ab').sub.2, Fv and SCA fragments which are capable of binding an epitopic determinant. Monoclonal antibodies are made from antigen containing fragments of the protein by methods well known to those skilled in the art (Kohler, et al., Nature, 256:495, 1975). An Fab fragment consists of a monovalent antigen-binding fragment of an antibody molecule, and can be produced by digestion of a whole antibody molecule with the enzyme papain, to yield a fragment consisting of an intact light chain and a portion of a heavy chain. An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner. An (Fab') .sub.2 fragment of an antibody can be obtained by treating a whole antibody molecule with the enzyme pepsin, without subsequent reduction. A (Fab').sub.2 fragment is a dimer of two Fab' fragments, held together by two disulfide bonds. An Fv fragment is defined as a genetically engineered fragment containing the variable region of a light chain and the variable region of a heavy chain expressed as two chains. A single chain antibody ("SCA") is a genetically engineered single chain molecule containing the variable region of a light chain and the variable region of a heavy chain, linked by a suitable, flexible polypeptide linker.

The terms "specifically binds" and "specific binding" when used in reference to the binding of an antibody to a target molecule (e.g., peptide) or to a target cell (e.g., immunosuppressive B cells), refer to an interaction of the antibody with one or more epitopes on the target molecule or target cell where the interaction is dependent upon the presence of a particular structure on the target molecule or target cell. For example, if an antibody is specific for epitope "A" on the target cell, then the presence of a protein containing epitope A (or free, unlabeled A) in a reaction containing labeled "A" and the antibody will reduce the amount of labeled A bound to the antibody. In various embodiments, the level of binding of an antibody to a target molecule or target cell is determined using the "IC50," i.e., "half maximal inhibitory concentration" that refer to the concentration of a substance (e.g., inhibitor, antagonist, etc.) that produces a 50% inhibition of a given biological process, or a component of a process (e.g., an enzyme, antibody, cell, cell receptor, microorganism, etc.). It is commonly used as a measure of an antagonist substance's potency.

Reference herein to "normal cells" or "corresponding normal cells" means cells that are from the same organ and of the same type as the cancer cell type. In one aspect, the corresponding normal cells comprise a sample of cells obtained from a healthy individual. Such corresponding normal cells can, but need not be, from an individual that is age-matched and/or of the same sex as the individual providing the cancer cells being examined. In another aspect, the corresponding normal cells comprise a sample of cells obtained from an otherwise healthy portion of tissue of a subject having non-small cell lung cancer (NSCLC), prostate cancer (PCa), pancreatic ductal adenocarcinoma (PDAC), renal cell carcinoma (RCC) and hepatocellular carcinoma (HCC).

As used herein, the term "platinoid" refers to a platinum-based chemotherapeutic agent known for treating cancer. Exemplary platinoid drugs include, but are not limited to, cisplatin, oxaliplatin, carboplatin, nedaplatin, triplatin tetranitrate, pheanthriplatin, picoplatin, and straplatin.

As used herein, the term "mimetic" refers to a molecule such as a small molecule, a modified small molecule or any other molecule that biologically mimics the action or activity of some other small molecule. As such, a platinoid mimetic refers to an agent that having the same or substantially the same biological action or activity as a platinoid.

As used herein, "checkpoint inhibitor therapy" refers to a form of cancer treatment immunotherapy that targets immune checkpoints, key regulators of the immune system that stimulate or inhibit its actions, which tumors can use to protect themselves from attacks by the immune system. Checkpoint therapy can block inhibitory checkpoints, restoring immune system function. Exemplary checkpoint inhibitors include, but are not limited to, ipilimumab (targeted to CTLA-4), nivolumab (targeted to PD-1), pembrolizumab (targeted to PD-1), atezolizumab (targeted to PD-L1), avelumab (targeted to PD-L1), and durvalumab (targeted to PD-L1).

As used herein, "immunosuppressive B cells," "immuno-suppressive plasmocyte cells," "immunosuppressive plasma cells," interchangeably refer to B lymphocyte cells that impede T-cell-dependent immunogenic chemotherapy and are characterized by expressing PD-L1 and Interleukin-10 (IL10' PD-L1.sup.+). In various embodiments, immunosuppressive B cells further express immunoglobulin A (IgA-.sup.+IL10.sup.+PD-L1.sup.+).

As used herein, "immunogenic cell death" or "ICD" refers to a form of cell death caused by some cytostatic agents such as oxaliplatin, cyclophosphamide, and mitoxantrone (Galluzzi et al., Cancer Cell. 2015 Dec. 14; 28(6):690-714) and anthracyclines, bortezomib, radiotherapy and photodynamic therapy (PDT) (Garg et al. (2010) "Immunogenic cell death, DAMPs and anticancer therapeutics: an emerging amalgamation". Biochim Biophys Acta 1805 (1): 53-71).

Unlike normal apoptosis, which is mostly nonimmunogenic or even tolerogenic, immunogenic apoptosis of cancer cells can induce an effective antitumour immune response through activation of dendritic cells (DCs) and consequent activation of specific T cell response. ICD is characterized by secretion of damage-associated molecular patterns (DAMPs).

As used herein, the terms "low dose" and "LD" refer to an amount or concentration of an agent that is sufficient to elicited minimal cell death in vitro (e.g., .ltoreq.10-15%) and does not cause tumor regression in vivo. Thus, for purposed of this disclosure, the term "low dose" may include a non-ICD amount of a cytostatic agent or a platinoid.

As used herein, the terms "programmed cell death 1 ligand 1 isoform a precursor" and "PD-L1" (also known as CD274; B7-H; B7H1; PDL1; PD-L1; PDCD1L1; PDCD1LG1) refer to the immune inhibitory receptor ligand that is expressed by hematopoietic and non-hematopoietic cells, such as T cells and B cells and various types of tumor cells. The encoded protein is a type 1 transmembrane protein that has immunoglobulin V-like and C-like domains. Interaction of this ligand with its receptor inhibits T-cell activation and cytokine production. During infection or inflammation of normal tissue, this interaction is important for preventing autoimmunity by maintaining homeostasis of the immune response. In tumor microenvironments, this interaction provides an immune escape for tumor cells through cytotoxic T-cell inactivation. Expression of this gene in tumor cells is considered to be prognostic in many types of human malignancies, including colon cancer and renal cell carcinoma. Alternative splicing results in multiple transcript variants.

The terms "interleukin 10" and "IL-10" (also known as CSIF; TGIF; GVHDS; IL10A) refer to a cytokine produced primarily by monocytes and to a lesser extent by lymphocytes. This cytokine has pleiotropic effects in immunoregulation and inflammation. It down-regulates the expression of Th1 cytokines, MHC class II Ags, and costimulatory molecules on macrophages. It also enhances B cell survival, proliferation, and antibody production The terms "immunoglobulin A," "IgA," and "Ig alpha" refer to the major immunoglobulin class in body secretions. It may serve both to defend against local infection and to prevent access of foreign antigens to the general immunologic system. Portions of human IgA amino acid sequences.

Unless defined otherwise, all technical and scientific terms used herein have the same meaning as commonly understood by one of ordinary skill in the art to which this invention belongs.

Although any methods and materials similar or equivalent to those described herein can be used in the practice or testing of the invention, the preferred methods and materials are now described.

Use of human pluripotent cell lines as a source of the astrocyte restricted precursor cells is covered by the invention. Human iPSC cells have been previously shown to differentiate into neuronal progenitors that subsequently generate differentiated neurons. In the present invention, dividing precursor cells that expressed neuronal or glial markers were first identified in ES cells. Differentiation conditions were similar to those described herein and used for generating neurons. Specifically, the first stage of differentiation of the ES cells was induced by the formation of embryonic bodies (EBs) in FBS media with or without 10.mu.M all trans-RA. After 4 days in suspension, EBs were plated onto fibronectin coated plates in defined proliferation media supplemented with 10 ng/mL hEGF, 10 ng/mL hbFGF, 1 ng/mL hPDGF-AA, and 1 ng/mL hIGF-1. In these conditions, the EBs adhered to the plates and cells began to migrate and proliferate on the plastic, forming a monolayer. After 3 days in these conditions many cells with neuronal morphology were present. Similar results were found with each human ES cell line. Multiple types of dividing cell populations can be identified in cultures of differentiating ES cells based on antibodies that recognize cell surface epitopes. These include A2B5+ cells, PSANCAM+ cells and CD44+ cells. Double labeling experiments following differentiation showed that the CD44+ cells of the ES cells were a unique population of cells that were similar morphologically, antigenically and in their ability to differentiate into astrocytes to the astrocyte restricted cells of the present invention isolated from other sources of neural tissue and cells.

In one aspect, the invention provides a method of treating cancer by increasing immunogenicity of dendritic cells through induction of a crosstalk between dendritic cells and astrocytes. In one embodiment the invention teaches that enhancement of immune-stimulating potency of astrocyte-dendritic cell cultures can be achieved by increasing expression of major histocompatibility complex (MHC) molecules on dendritic cells. The method includes contacting the dendritic cell with an effective amount (e.g., a low dose or low concentration) of a HAT activator, such as a platinoid, thereby inducing expression of MHC molecules on the dendritic cell. In various embodiments, the method may further include inducing cell death of the astrocyte cell when combined with the dendritic cell. Likewise, the invention provides for use of an effective amount of a HAT activator, such as a platinoid, to induce expression of MHC molecules on a dendritic cell. The methods and uses may be practice in vivo, in vitro or ex vivo. It is known that certain chemotherapeutic drugs, including Oxali, are immunostimulatory when used in low, non-lymphoablative doses. The molecular basis for this effect has been enigmatic and was attributed to immunogenic cell death, a unique form of apoptosis that is immunostimulatory rather than immunosuppressive. Although its mechanistic basis remains obscure, ICD can facilitate antigen release and T-cell priming, the first step in the cancer-immunity cycle. The results provided herein, however, show that Oxali acts within malignant tumor cells, potentiating their ability to process and present class I antigens, thereby enhancing their recognition and eventual killing by reinvigorated CTLs. This activity is also exhibited by other platinoids, albeit to a considerably lower extent, and may explain why the efficacy of the anti-PD-L1+Carbo combination in human NSCLC correlates with enhanced MHC-I component expression. The induction of MHC-I associated genes by low dose Oxali correlates with relaxation of their regulatory regions and increased transcription factor accessibility, a response that usually depends on histone acetylation.

The utilization of dendritic cells for immunotherapy has previously been described in various cancer types such as melanoma. In addition, other cancers have been treated with dendritic cells [1-125].

In some embodiments of the invention, astrocytes are generated from stem cells or progenitor cells. One type of stem cell is mesenchymal stem cells. For the practice of the invention, MSC are used generate astrocytes. "Mesenchymal stem cell" or "MSC" in some embodiments refers to cells that are (1) adherent to plastic, (2) express CD73, CD90, and CD105 antigens, while being CD14, CD34, CD45, and HLA-DR negative, and (3) possess ability to differentiate to osteogenic, chondrogenic and adipogenic lineage. Other cells possessing mesenchymal-like properties are included within the definition of "mesenchymal stem cell", with the condition that said cells possess at least one of the following: a) regenerative activity; b) production of growth factors; c) ability to induce a healing response, either directly, or through elicitation of endogenous host repair mechanisms. As used herein, "mesenchymal stromal cell" or ore mesenchymal stem cell can be used interchangeably. Said MSC can be derived from any tissue including, but not limited to, bone marrow, adipose tissue, amniotic fluid, endometrium, trophoblast-derived tissues, cord blood, Wharton jelly, placenta, amniotic tissue, derived from pluripotent stem cells, and tooth. In some definitions of "MSC", said cells include cells that are CD34 positive upon initial isolation from tissue but are similar to cells described about phenotypically and functionally. As used herein, "MSC" may includes cells that are isolated from tissues using cell surface markers selected from the list comprised of NGF-R, PDGF-R, EGF-R, IGF-R, CD29, CD49a, CD56, CD63, CD73, CD105, CD106, CD140b, CD146, CD271, MSCA-1, SSEA4, STRO-1 and STRO-3 or any combination thereof, and satisfy the ISCT criteria either before or after expansion. Furthermore, as used herein, in some contexts, "MSC" includes cells described in the literature as bone marrow stromal stem cells (BMSSC), marrow-isolated adult multipotent inducible cells (MIAMI) cells, multipotent adult progenitor cells (MAPC), mesenchymal adult stem cells (MASCS), MultiStem®, Prochymal®, remestemcel-L, Mesenchymal Precursor Cells (MPCs), Dental Pulp Stem Cells (DPSCs), PLX cells, PLX-PAD, AlloStem®, Astrostem®, Ixmyelocel-T, MSC-NTF, NurOwn™, Stemedyne™-MSC, Stempeucel®, StempeucelCLI, StempeucelOA, HiQCell, Hearticellgram-AMI, Revascor®, Cardiorel®, Cartistem®, Pneumostem®, Promostem®, Homeo-GH, AC607, PDA001, SB623, CX601, AC607, Endometrial Regenerative Cells (ERC), adipose-derived stem and regenerative cells (ADRCs).

Mesenchymal stem cells (MSCs) are adult stem cells with self-renewing abilities[126] and have been shown to differentiate into a wide range of tissues including mesoderm- and nonmesoderm-derived[126, 127], such as hepatocytes[128-133]. MSCs are capable of entering and maintaining satellite cell niches, particularly in hematopoiesis[134, 135], and are key in tissue repair and regeneration, aging, and regulating homeostasis[136-139]. In the case of heart failure, MSCs can aid in regeneration of cardiac tissue[140-146], and their interactions with the immune system[147-153] have potential as adjuvants during organ transplants[154], including cardiac transplantation[155].

MSCs were discovered in 1970 by Friedenstein et al[156] who demonstrated that bone marrow (BM) contained both hematopoietic stem cells (HSCs), which are non-plastic adherent, and a population of a more rare adherent cell. The adherent cells were able to form single cell colonies and were referred to as stromal cells. Those stromal cells, which are capable of self-renewal and expansion in culture are now referred to as mesenchymal stem cells (MSCs). Friedenstein was the first to show that MSCs could differentiate into mesoderm and to demonstrate their importance in controlling the hematopoietic niche [157].

In the 1980s, more research on MSCs found that they could differentiate into muscle, cartilage, bone and adipose-derived cells [158]. Caplan et al showed that MSCs are responsible for bone and cartilage regeneration induced by local cuing and genetic potential[159].

In the 1990s, Pittenger et al isolated MSCs from bone marrow and found that they retained their multilineage potential after expanding into selectively differentiated adipocytic, chondrocytic, or osteocytic lineages[127]. Likewise, Kopen et al showed that bone marrow MSCs differentiated into neural cells when exposed to the brain microenvironment[160]. In 1999, Petersen et al found that bone marrow-derived stem cells could be a source of hepatic oval cells in a rat model[161]. Specifically, they used male to female bone marrow transplant and subsequently induced blockade of hepatocyte proliferation by administration of a hepatotoxin followed by partial hepatectomy. As previously described, this procedure stimulates proliferation of LPC or "reserve cells" which generate new hepatocytes, such cells having previously identified as oval cells. Subsequent to the hepatectomy, Y chromosome, dipeptidyl peptidase IV enzyme, and L21-6 antigen were used to identify the newly generated oval cells, and their hepatocytic progeny to be of bone marrow origin.

The first decade of the $21^{st}$ century saw a surge of research on MSCs, leading to a greater understanding of their nature and of the cellular process behind regeneration [126, 138, 139]. In 2005, Teratani et al identified growth factors allowing hepatic fate-specification in mice and showed that embryonic stem cells could differentiate into functional hepatocytes [162]. A unique property of MSC is their apparent hypoimmunogenicity and immune modulatory activity [163], which is present in MSC derived from various sources [164]. This is believed to account for the ability to achieve therapeutic effects in an allogeneic manner. Allogeneic bone marrow derived MSC have been used by academic investigators with clinical benefit treatment of diseases such as graft versus host (GVHD) [165-170], osteogenesis imperfecta [171], Hurler syndrome, metachromatic leukodystrophy [172], and acceleration of hematopoietic stem cell engraftment [173-175]. The company Athersys has successfully completed Phase I safety studies using allogeneic bone marrow MSCs is now in efficacy finding clinical trials (Phase II and Phase III) for Multiple Sclerosis, Crohn's Disease, and Graft Versus Host Disease using allogeneic bone marrow derived MSC. Intravenous administration of allogeneic MSCs by Osiris was also reported to induce a statistically significant improvement in cardiac function in a double-blind study [176].

Currently there several MSC-based therapies that have received governmental approvals including Prochymal™ which was registered in Canada and New Zealand for treatment of graft versus host disease [177, 178]. Although in terms of clinical translation bone marrow MSC are the most advanced, several other sources of MSC are known which possess various properties that may be useful for specific conditions. Bone marrow is also a source for hematopoietic stem cells (HSCs), which have also been used for cardiac regeneration. Likewise, human placenta is an easily accessible source of abundant MSCs, which can be differentiated in vitro. Finally, MSCs with tissue regenerative abilities can also be isolated from adipose tissue and induced to hepatocytes in large numbers.

In some embodiments astrocytes are generated for culture with dendritic cells using a method comprising the steps of: (A) preparing astrocyte-like cells from stem cells, and (B) culturing said astrocyte-like cells prepared by the process (A) to provide culture supernatant, wherein said culture supernatant is added to dendritic cells. Said process (A) may include, but is not limited to, the steps of: 1) differentiating stem cells into neural stem cells using the astrocyte-conditioned medium, 2) proliferating said neural stem cells, and 3) inducing selective differentiation of said proliferated neural stem cells into astrocyte-like cells. In the above step 1), differentiation of stem cells to neural stem cells can be accomplished by, for example, culturing stem cells in an astrocyte-conditioned medium. Optionally, in the above step 1), a synthetic medium containing a basal medium supplemented with some factors such as growth factors and cytokines, or chemically-defined components may be mixed with said astrocyte-conditioned medium or a medium equivalent to said astrocyte-conditioned medium. In the method of the present invention, once astrocyte-like cells derived from stem cells are established, the astrocyte-like cells-conditioned medium prepared by culturing said astrocyte-like cells derived from embryonic stem cells may be used instead of the astrocyte-conditioned medium. The astrocyte-like cells-conditioned medium of the present invention may continuously be prepared by employing thus obtained astrocyte-like cells-conditioned medium of the present invention. In a preferred embodiment of the present invention, the step 1) is replaced by the step 1'): 1') differentiating stem cells to neural stem cells using a conditioned medium of astrocyte-like cells derived from stem cells. The differentiation in said steps 1) and 1') can be induced, for example, by culturing the cells in suspension culture. More specifically, in said step 1) or 1'), whole undifferentiated colonies of stem cells are cultured in suspension to provide cell spheres (so-called "Neural stem sphere(s)"; NSS), wherein a number of neural stem cells are preferably localized on the surface of said NSS. "Neural stem cell" as used herein refers to a precursor cell which differentiates into astrocyte-like cells and can be identified as positive cells expressing neural stem cells' markers such as nestin and musashi as well as glial precursors' markers such as A2B5. Any culture vessels having suitable shape and size for maintaining stable continuous suspension culture in the manner that the cell spheres (i.e. NSS) do not adhere to the bottom of the culture vessel may be used for this step. Examples of such culture vessels include a dish for suspension culture and petri dish for bacterial culture. Optionally, said culture vessel may be coated with 0.5% by weight of agarose to prevent the adhesion of the cell spheres to the bottom. The period for the suspension culture may be determined depending on the type of the embryonic stem cells. For example, the period for the suspension culture can be determined based on the appearance of neural stem cells which are astrocyte precursor cells on the surface of the NSS. Said neural stem cells can be detected, for example, based on the expression of neural stem cells' markers such as nestin and musashi or of glial precursors' marker such as A2B5. In addition, the efficacy of inducing differentiation into neural cells in suspension culture may be examined by detecting the expression of immature neural markers, such as .beta.III tubulin, using immunohistochemical techniques. Typical examples of the periods for culture are as follows; usually 1-10 days, preferably about 4 days (e.g. 3-5 days) for mouse embryonic stem cells, usually 1-15 days, preferably about 7 days (e.g. 5-8 days) for primate (including monkey, human) stem cells. Next step is the proliferation of the neural stem cells [step 2]. In said step 2), the neural stem cells prepared by above mentioned step 1) itself or NSS including said neural stem cells are cultured in an adherent culture system. Neural stem cells are proliferated by conducting said step 2). In addition, when NSS including neural stem cells are cultured in the manner as above, neural stem cells are migrated from the adhered NSS and proliferated around the NSS. Accordingly, a large amount of neural stem cells are proliferated by conducting said step 2) and thereby a large amount of astrocyte-like cells can be prepared in the following step 3). Examples of mediums suitable for proliferating neural stem cells in adherent culture of the NSS in the above mentioned step 2) include DMEM: F-12(1:1) and Neurobasal™ Medium (Invitogen Corporation) which are supplemented with B27 supplement [Brewer, G. J., Focus, 16, 6-9 (1994); Brewer, G. J., J. Neurosci. Res., 35, 567-576 (1993)] [Invitrogen Corporation, Catalog No: 17504-044] and proliferative/growth factors such as basic fibroblast growth factor (bFGF) and epidermal growth factor (EGF). Specifically, neural stem cells can be proliferated in an adherent culture system using Neurobasal Medium containing B27 supplement, bFGF, and optionally EGF, or DMEM: F-12 (1:1) containing N2 supplement, bFGF, and optionally EGF. Preferably, the culture vessel used for the adherent culture of the neural stem cells is coated with Matrigel™, (made by BD Bioscience), poly-L-lysine, laminin or the like, so as to facilitate the adherence of NSS or the moved and proliferated neural stem cells on the vessel as well as to maintain the conditions of neural stem cells stably. When using Matrigel™, the coating of said culture vessels may be conducted according to the manufacture's instructions. When using the other extracellular substratum, the coating may be applied by a conventional method. For example, a solution containing the extracellular substratum may be applied to the vessel so that the bottom of the culture vessel is covered well and then the vessel is allowed to stand for a certain period or is incubated at 37.degree. C. In case of using said proliferative/growth factors such as bFGF and EGF, the concentration of the factors may appropriately be determined depending on the type of the embryonic stem cells or the like. In case of bFGF, the desirable concentration is 1-200 ng/ml, preferably 20-40 ng/ml. In case of EGF, desirable concentration is 10-50 ng/ml, preferably 10-20 ng/ml. Alternatively, in case of combined use of bFGF and EGF, they may be mixed to be 10-20 ng/ml of bFGF and 10-20 ng/ml of EGF. The period for the above-described adherent culture may be determined depending on the type of animals from which the embryonic stem cells are derived, the degree of differentiation or the like. In the above mentioned step 2), further proliferation of neural stem cells can be achieved by detaching the moved and proliferated neural stem cells from the culture vessel and dissociating the cells individually using a cell-dispersant, for example, an enzyme such as trypsin, dispase, collagenase, papain or the like, EDTA, or cell dissociation buffer [Gibco-Invitrogen], and then subculturing the dissociated cells in freshly prepared culture system. Specifically, for example, 0.05-0.35% by weight of trypsin may be used to detach the moved and differentiated neural stem cells and to dissociate the same individually. Thus dissociated cells may be subcultured and proliferated further. In the step, undifferentiated embryonic stem cells located in the center of the cell population may optionally be eliminated from the culture to decrease the contamination of cells, such as undifferentiated embryonic stem cells, other than neural stem cells and increase the abundance ratio of the neural stem cells. Next is the step of inducing differentiation of neural stem cells proliferated in step 2) selectively into astrocyte-like cells[step 3]. The condition for the selective induction of differentiation into astrocyte-like cells can be defined depending on the type of the starting embryonic stem cells.

For example, it can be achieved by replacing the medium used in said step 2) with a medium containing no proliferative/growth factors such as bFGF and EGF. Astrocyte-like cells derived from embryonic stem cells can be prepared as a population including the cells expressing GFAP by conducting the steps 1)-3) of the above mentioned step (A). Next is the step of culturing astrocyte-like cells derived from embryonic stem cells, which is prepared by the step (A) and then, obtaining the culture supernatant[step (B)]. In the step (B), conditions for culturing astrocyte-like cells derived from embryonic stem cells are not limited as long as said astrocyte-like cells are able to survive and various factors can be released from said astrocyte-like cells.

Using serum free medium is preferable when preventing a contamination of cell components derived from other animals is required for the process of manufacture. Specifically, for example, DMEM:F-12 medium containing N2 supplement (.times.1: 5 .mu.g/ml insulin, 10.mu.g/ml transferrin, 63 ng/ml progesterone, 16.11.mu.g/ml putrescine and 2 ng/ml selenite) is employed and cells are cultured at 37.degree. C., about 5% CO.sub.2.

For generation of dendritic cells, numerous means are known to one of skill in the art. These include generation from inducible pluripotent stem cells, to generation from CD34 positive hematopoietic stem cells, to adherent monocyte derived cells. One embodiment dendritic cells are generated as below:

Monocyte Proliferating Culture Medium: The monocyte proliferating culture medium of the present invention contains at least one of Flt-3L, IL-3, and IFN-.gamma. and is used before treatment for differentiating monocytes into dendritic cells. Specifically, the monocyte proliferating culture medium can further contain a nutritional component, a pH adjuster, and other components for enabling culture of monocytes. The culture medium containing such components is not particularly limited, and examples thereof include serum-free synthetic culture media for lymphocytes, AIM-V, and RPMI-1640. The term "culture medium" throughout the specification encompasses media in liquefied prepared forms and also component mixtures (usually powder) before preparation. The monocyte proliferating culture medium of the present invention may further contain a cytokine (granulocyte macrophage colony-stimulating factor (GM-CSF)) involved in differentiation of monocytes. A monocyte tends to differentiate into a macrophage in the presence of GM-CSF and tends to differentiate into a dendritic cell in the presence of GM-CSF and IL-4. The investigation by the present inventors, however, revealed a fact that the monocyte proliferating culture medium of the present invention containing GM-CSF can considerably accelerate proliferation of monocytes. It has been conventionally known that GM-CSF itself also has an effect of allowing proliferation of monocytes, however, the monocyte proliferating culture medium of the present invention containing GM-CSF can considerably accelerate proliferation of monocytes without differentiating the monocytes. In addition, the monocyte proliferating culture medium of the present invention may further contain IL-4 in an amount less than the amount allowing differentiation of monocytes into dendritic cells (e.g., 500 to 2000 IU/mL), in addition to GM-CSF. The amount of GM-CSF contained in the monocyte proliferating culture medium of the present invention is, for example, within a range of 500 to 2000 IU/mL. The monocyte proliferating culture medium of the present invention may contain a reagent that is usually used in cell culture. Examples of the reagent include antibiotics (e.g., gentamycin and kanamycin), albumin, and serum (e.g., fetal bovine serum). The monocyte proliferating culture medium of the present invention may contain autologous plasma (i.e., the monocytes to be proliferated and the autologous plasma are collected from the same body) derived from a living body (mammals such as human, porcine, bovine, horse, goat, sheep, rabbit, kangaroo, or monkey). Furthermore, the monocyte proliferating culture medium of the present invention may contain a material for accelerating differentiation induction to dendritic cells, such as picibanil chloride or prostaglandin E2 (PGE2). Method of Producing Monocytes The method of producing monocytes of the present invention includes a proliferation step of culturing a monocyte material in the monocyte proliferating culture medium of the present invention to allow the monocytes to proliferate. Proliferation Step The proliferation step according to the present invention may be performed under any condition without particular limitation, and from the viewpoint of allowing monocytes to proliferate before the start of differentiation of a lot of monocytes, the culture is preferably performed under conditions of 30.degree. C. to 40.degree. C. and 2% to 8% CO.sub.2. The period of culture time can be appropriately controlled depending on the necessary amount of monocytes and may be 3 to 20 days, 3 to 18 days, 3 to 14 days, or 3 to 10 days. During the culture, replacement of the culture medium may be appropriately carried out by a known method. According to the method of producing monocytes of the present invention, the monocytes in a monocyte material can proliferate to an amount allowing clinical use (e.g., 10.sup.6 to 10.sup.7 cells/mL or more) within a short culture time such as 14 days. The amount allowing clinical use refers to an amount of monocytes proliferated such that a dendritic cell vaccine prepared from dendritic cells differentiated from the proliferated monocytes can be directly used as a vaccine without being subjected to freezing treatment. In the method of producing monocytes of the present invention, monocytes are cultured in the monocyte proliferating culture medium of the present invention, that is, monocytes are proliferated under conditions giving a less burden on the monocytes.

Consequently, the method of producing monocytes of the present invention can be expected to provide monocytes with a high vital cell ratio (e.g., higher than 90%). Monocyte Material The monocyte material in the present invention is a specimen containing monocytes. The monocyte material may be composed of monocytes only. Alternatively, since the method of producing monocytes of the present invention can allow selective and efficient proliferation of monocytes, the monocyte material may be a mixture containing monocytes and a leukocyte component (e.g., lymphocytes, NK cells, or NKT cells) other than monocytes. This mixture may further contain plasma and erythrocytes. The mixture may be a mononuclear cell fraction mainly containing monocytes and lymphocytes prepared from a body fluid sample such as blood by, for example, density gradient centrifugation. It is preferred to perform the reduction step for preparing the monocyte material by reducing the content of components other than monocytes in the body fluid, before the proliferation step. The reduction can be performed by, for example, a method using a magnetic bead, density gradient centrifugation, a method of isolating monocytes in components of body fluid by means of adhesion of only the monocytes to a petri dish, or a combination thereof. The magnetic bead can collect monocytes simply and with a high yield and causes less damages to the monocytes. Its use is therefore preferred. The magnetic bead has a higher affinity to monocytes or at least one (preferably all) of leukocyte components other than monocytes, plasma, erythrocytes in the monocyte material than the others. Such a magnetic bead may have a structure in which, for example, an antibody to the material to be isolated is bound to a magnetic carrier. If a mononuclear cell fraction prepared by density gradient centrifugation of body fluid is treated with a magnetic bead, the yield of monocytes is advantageously further increased. Use of a magnetic bead having a relatively high affinity to monocytes can mainly isolate monocytes from body fluid (this is referred to as monocyte positive selection). A monocyte material is obtained by removing the magnetic bead from the isolated monocytes by a known method. This embodiment is advantageous in the point that the number of types of necessary magnetic beads is small, but it needs a step of removing the magnetic beads from monocytes, and damage to the monocytes is slightly worried. Use of a magnetic bead having a relatively high affinity to at least one of leukocyte components other than monocytes, plasma, and erythrocyte can remove components other than monocytes from body fluid (this is referred to as monocyte negative selection). As a result, a monocyte material mainly containing monocytes is prepared. This embodiment is disadvantageous in the point that the number of types of necessary magnetic beads is large, but it does not need a step of removing the magnetic beads from monocytes and can certainly provide good quality monocytes and is therefore preferred. The sample to be subjected to the monocyte negative selection may be a mononuclear cell fraction prepared by density gradient centrifugation of body fluid. In this case, a magnetic bead having a relatively high affinity to lymphocytes is used. In a case of using a magnetic bead, a magnetic cell separator can be used. The magnetic cell separator isolates monocytes from body fluid based on a predetermined program by setting reagents such as a magnetic bead, together with a body fluid sample such as blood, in the separator. The use of such an apparatus can isolate monocytes from body fluid rapidly and with a high yield and is therefore preferred. Isolation of monocytes with a high yield can significantly increase the proliferation efficiency of monocytes with the monocyte proliferating agent of the present invention. A preferable example of the magnetic cell separator in the present invention is "RoboSep (trademark)" (VERITAS Corporation). Body Fluid Examples of samples to prepare the monocyte material include body fluid such as blood and bone marrow fluid. The blood is collected from a living body (e.g., a human cancer patient), and examples thereof include peripheral blood and cord blood. In particular, peripheral blood is preferred from the viewpoint of reducing the burden on the subject. The body fluid may be collected by any method without particular limitation and may be collected from a region such as an arm, wrist, or foot using, for example, a syringe or winged needle. Since the method of producing monocytes of the present invention can be performed with a small amount of body liquid, the burden (e.g., cost and time) on the living body from which the body fluid is collected is significantly low, compared to conventional methods such as apheresis.

Conventionally, in order to produce a dendritic cell vaccine, a large amount, such as 300 to 400 mL, of blood has been collected from a living body. In the method of producing monocytes of the present invention, however, the amount of body fluid used may be small, such as 100 mL or less, 90 mL or less, 80 mL or less, 70 mL or less, 60 mL or less, 50 mL or less, 40 mL or less, 35 mL or less, 30 mL or less, 25 mL or less, 20 mL or less, 15 mL or less, 10 mL or less, 5 mL or less, 1 mL or less, or 0.5 mL or less. The lower limit of the amount of body fluid is not particularly determined and may be 0.1 mL or more for example.

The monocytes prepared by the method of producing monocytes of the present invention may be directly differentiated into dendritic cells through a differentiation step or may be cryopreserved by a conventionally known method. The cryopreserved monocytes can be subjected to the differentiation step of monocytes after thawing. However, from the viewpoint of avoiding a loss of monocytes that can be differentiated, the monocytes preferably are not cryopreserved. In the present invention, since monocytes for being subjected to the differentiation step can be obtained without performing repetition of culture of monocytes several times, the monocytes can be supplied to the differentiation step of the monocytes without undergoing cryopreservation.

The method of producing dendritic cells of the present invention includes a monocyte production step of producing monocytes by the method of producing monocytes of the present invention and a differentiation step of differentiating the monocytes prepared in the monocyte production step into dendritic cells. Differentiation Step The method of differentiating monocytes into dendritic cells is a conventionally known step. That is, monocytes are differentiated into immature dendritic cells by culture in a culture medium for differentiation containing, for example, IL-4.

The resultant immature dendritic cells are differentiated into mature dendritic cells by culture in a culture medium containing, for example, TNF-.alpha.. The term "dendritic cell" in the present invention encompasses both an immature dendritic cell and a mature dendritic cell. Also in the differentiation step of the present invention, a culture medium containing at least one of Flt-3L, IL-3, and IFN-.gamma. is preferably used. Such a culture medium allows differentiation of monocytes into dendritic cells while allowing proliferation of monocytes, resulting in production of a larger number of dendritic cells. However, when a sufficient number of monocytes can be prepared in the proliferation step or when the necessary number of dendritic cells is not large, the culture medium may not contain the above-mentioned components. Pulse Step Dendritic cells capable of presenting a desired antigen can be prepared by incorporating, for example, a material (e.g., peptide) extracted from cancer cells, a cancer-specific antigen, or an artificial antigen into the resulting immature dendritic cells or mature dendritic cells (pulsing with such a material).

The pulse step may be performed during the process of producing dendritic cells or may be performed during the process of preparing a vaccine after the production of dendritic cells as described below. The method of pulsing is not particularly limited as long as a desired antigen is incorporated into dendritic cells and is performed by, for example, culturing dendritic cells in the presence of a desired antigen. In general, an antigen is incorporated into immature dendritic cells easier than into mature dendritic cells. The pulsing is therefore preferably performed using immature dendritic cells. Whether the resulting cells are dendritic cells or not is confirmed by analysis of a cell surface marker of dendritic cells by flow cytometry. The cell surface marker of the dendritic cell is, for example, CD83. A cell having such a marker is recognized to be a dendritic cell. Whether the dendritic cells prepared by the method of producing dendritic cells of the present invention have antigen-presenting ability or not is confirmed by analysis of a cell surface marker of dendritic cells by flow cytometry. Examples of the cell surface marker of the dendritic cell having antigen-presenting ability include MHC class I molecules (HLA-A, B, and C) and MHC class II molecules (HLA-DR). A dendritic cell having such a marker is recognized to have antigen-presenting ability. Method of Producing a Dendritic Cell Vaccine The method of producing a dendritic cell vaccine of the present invention includes a dendritic cell-producing step of producing dendritic cells by the method of producing dendritic cells of the present invention and a preparation step of preparing a dendritic cell vaccine from the dendritic cells produced in the dendritic cell-producing step. Preparation Step The dendritic cell vaccine may be prepared from dendritic cells by any method without particular limitation. For example, the dendritic cells are mixed with an agent (such as physiological saline or a Ringer solution) that is commonly formulated in a vaccine preparation. When dendritic cells not yet subjected to the pulse step are used, the dendritic cells are subjected to the pulse step. The method of producing a dendritic cell vaccine of the present invention may not include a cryo-preservation step of cryopreserving at least one of the monocytes and the dendritic cells. In the method of producing a dendritic cell vaccine of the present invention, a sufficient amount of monocytes or dendritic cells for producing a dendritic cell vaccine can be prepared in a short period of time, and a dendritic cell vaccine can be timely prepared without requiring a store of monocytes or dendritic cells. Therefore, monocytes or dendritic cells optionally produced can be used without subjecting to cryopreservation for producing a dendritic cell vaccine. Consequently, damage of cells and a reduction in antigen-presenting ability of the dendritic cells by freezing can be avoided. The resulting dendritic cell vaccine can be administered in vivo by a conventionally known method such as intradermal injection. The monocyte material is preferably prepared from body fluid collected from a subject to which the dendritic cell vaccine is administered. The dendritic cell vaccine reduced in harmful side effects can be prepared by using a monocyte material derived from a subject to which the dendritic cell vaccine is administered. However, as long as the immune reaction occurring by administration of the dendritic cell vaccine is acceptable, body fluid collected from a subject other than the subject to which the vaccine is administered may be used.

Example 1: Generation of Immunogenic Co-Culture Stimulates Enhanced Proliferative Response Human neural progenitor cells were purchased from All-cells. Frozen aliquots of cells were thawed and plated on fibronectin/laminin-coated multiwell dishes in Neural Progenitor Cell Basal Medium (NPBM, Cambrex) supplemented with human recombinant basic fibroblast growth factor, human recombinant epidermal growth factor, "neural survival factors", 5 mg/mL gentamicin, and 5 mg/mL amphotericin-B (Singlequots, Cambrex). Cultures were incubated at 37.degree. C., 5% CO.sub.2 and fixed 24 hours later. These wells were subsequently processed for immunocytochemistry to assess the starting population of Cambrex cells. In parallel, Cambrex cells were thawed and immediately plated on fibronectin/laminin-coated flasks (Greiner) and cultured in Neuroepithelial Precursor (NEP) medium that consisted of DMEM-F12 (Life Technologies) supplemented with additives as described by Bottenstein and Sato, basic fibroblast growth factor (bFGF, 10 ng/ml, Peprotech, Rocky Hill, N.J.), and chick embryo extract (CEE, 10%). Unattached cells typically formed floating spheres. After 24 hours in culture, spheres were removed, gently triturated, and re-combined with the attached cells. NEP media was exchanged every other day. After 5 days in culture, immunopanning and flow-activated cell sorting were used to remove ENCAM+, NG2+, and A2B5+ cells. Briefly, cells were treated with 5 mM EDTA (Life Technologies) and the suspension plated on an ENCAM antibody (5A5, Developmental Studies Hybridoma Bank)-coated dish to allow binding of all ENCAM+ cells to the plate. ENCAM antibody-coated dishes were prepared by sequentially coating tissue culture dishes with an unlabeled anti-mouse IgM antibody (10 mg/ml) overnight, rinsing dishes with DPBS, followed by coating with 5A5 hybridoma supernatant for 1-3 hours at 37.degree. C. Plates were washed twice with DPBS prior to plating neural progenitor cells. After a 30 minute exposure period, unbound cells (eNCAM-cells) were removed and plated onto a dish coated with antibodies to NG2 for 30 minutes. NG2 panning dishes were made by coating dishes with an NG2 antibody (1:100) for 1-3 hours at 37.degree. C. The supernatant was then removed (ENCAM-/NG2-cells) and immunostained for A2B5. Cells were exposed to antibodies to A2B5 (1:2, Developmental Studies Hybridoma Bank) in NEP media for 1 hour at 37.degree. C., 5% CO.sub.2. A secondary goat anti-mouse IgM-PE labeled antibody was then applied for 1 hour to stain the membranes of live A2B5+ cells. All cells were then sent through a flow-activated cell sorter to remove the population of A2B5+ cells. After sorting, the negative population (human NEPs) was propagated in NEP media on fibronectin/laminin coated T-75 flasks prior to transplantation studies. NEP media was exchanged every other day. Panned/sorted populations of human NEPs were plated on fibronectin/laminin-coated 12 mm coverslips in various conditions to promote differentiation. To induce neuronal differentiation, cells were exposed to bFGF (10 ng/ml) and NT3 (10 ng/ml, Peprotech). After 5 days in culture, fixed cultures were stained using antibodies to beta-III tubulin to assess the capacity of these cells to differentiate into neurons. For oligodendrocyte differentiation, cells were plated in a bFGF (10 ng/ml)-containing medium for 2 days and then were switched to a medium containing PDGF (10 ng/ml, Upstate Biotech., Waltham, Mass.) and T3 (50 nM) for 7 days. Antibodies to 04, GalC and MBP were used to identify oligodendrocytes in culture. For astrocytic differentiation, cells were cultured for 5 days in the presence of fetal calf serum (10%, Life Technologies).

Mixed cell cultures of human fetal cells (12-22 weeks of gestation) were obtained from Clonetics and plated in T80 flasks in the presence of bFGF and CEE (10%). After 3 days in culture cells were labeled with A2B5 and NG-2. Immunonegative cells were collected by FACS sorting analysis and replated into flasks in the presence of bFGF and CEE. After 24 hours cells were labeled with E-NCAM, sorted by FACS and negative cells were replated at a clonal density in 10 cm dishes in the presence of bFGF and CEE. Control dishes were labeled after 24 hours with A2B5, E-NCAM, GFAP and NG-2. At that time point, 97% of all cells do not express any of the differentiation markers tested. Single cells were grown at a clonal density of 50-200 cells/35 mm dish). Cells were maintained in FGF and CEE for 8-10 days and then CEE was withdrawn to initiate differentiation. For oligodendrocyte differentiation cultures were exposed to PDGF and thyroid hormone. After 5-7 days cultures were labeled with antibodies against GFAP and beta-III tubulin to determine differentiation into astrocytes and neurons, respectively. Generation of oligodendrocytes was assessed 7 to 15 days after the initiation of differentiation. Neuronal and glial differentiation was assessed using antibodies against GFAP, and beta-III tubulin. For oligodendrocyte differentiation, cultures were exposed to PDGF and thyroid hormone and differentiation was assessed using antibodies to 04 and Gal-C.

Isolated astrocytes were incubated at a 1:1 ratio with monocyte derived dendritic cells. Dendritic cells were generated by culture of adherent monocytes with 4 days of IL-4 and GM-CSF at a concentration of 10 ng per ml. Cells were pulsed with 10 micrograms of hen egg while lysosome on day 7 of culture, treated with lps at 10 pg/ml and administered to BALB/c mice intradermally at 100,000 cells per mouse. At the indicated timepoints splenocytes were extracted and incubated with HEL at 10 ng/well for 48 hours. Proliferation was assessed by tritiated thymidine incorporation. Results are shown in FIG. 1.

Figure 2:
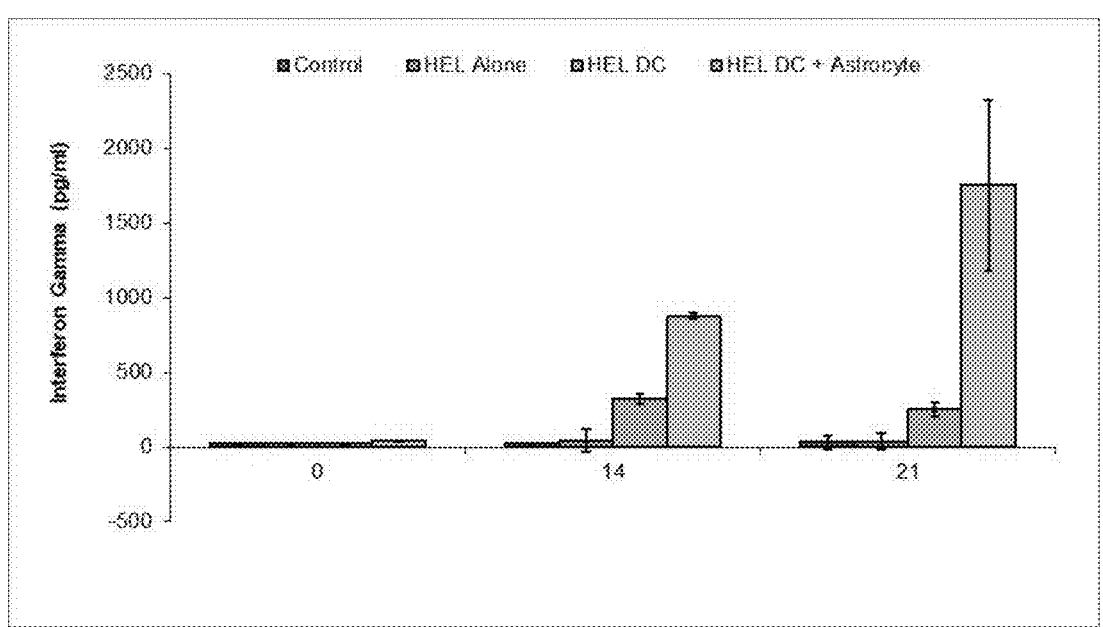
FIG. 2 is a bar graph showing the Interferon Gamma levels of HEL alone, HEL DC, and HEL DC and Astrocytes

Example 2: Generation of Immunogenic Co-Culture Stimulates Enhanced Interferon Gamma Response Mice were treated as in Example 1 and interferon gamma response was assessed as a marker of Th1 recall immunity. Results are shown in FIG. 2.

Figure 3:
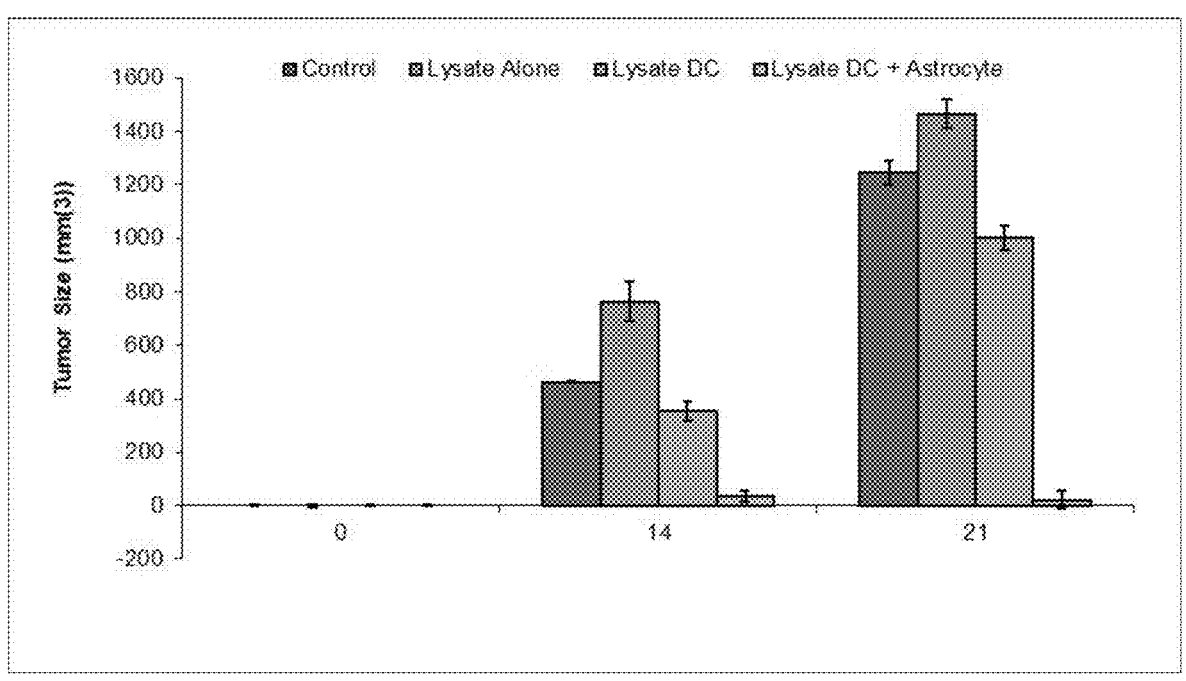
FIG. 3 is a bar graph showing the tumor size of mice based on Lysate alone, Lysate DC, and Lysate DC and Astrocytes

Example 3: Generation of Immunogenic Co-Culture Stimulates Inhibition of Breast Cancer BALB/c mice were treated as in Example 1 with exception that dendritic cells were loaded with 4T1 lysate. Mice were inoculated at day 0 with 1 million 4T1 cells. Tumor growth was assessed as indicated. All experiments had groups of 10 mice per endpoint. Results are shown in FIG. 3.

Example 4: Suppression of Melanoma Using Astrocyte and Dendritic Cell Immunotherapy The neuron culture for transplantation was differentiated from the iPSCs of a healthy donor (without neurological pathologies), which were derived from the skin fibroblasts of a male donor (age, 60 years) who had signed an informed consent. iPSC were created using the Nucleofector™ technology purchased from Lonza. The iPSCs were detached from the substrate using a trypsin solution and seeded at a density of 40,000 cells/cm2 in a mTeSR1 medium supplied with a 5 μM ROCK inhibitor. Upon reaching a density of about 80-90%, the mTeSR1 medium was replaced with a neuronal differentiation medium (14 days, medium change every other day). The produced neural progenitors were detached from the substrate with a Versen solution via incubation of the cells in a CO2 incubator at 37° C. for 10 min and centrifuged at 240 g for 5 min. The cells were plated (at a density of 4×105 cells/cm2) onto Matrigel-coated Petri dishes and cultured in a neural progenitor culture medium for 10 days (medium change every other day). After 10 days, the cells were passaged (4×105 cells/cm2) and cultured in the same medium. At the second passage, the cells were detached from the substrate using a 0.01% trypsin solution which was inactivated with a DMEM medium containing 10% fetal bovine serum. The cells in suspension were counted, washed with physiological saline (centrifuged at 240 g for 5 min), re-suspended in saline to a concentration of 3.5×105 cells per 10 μL, and used for the transplantation. The cell dose chosen for the transplantation into the rat striatum was consistent with that reported earlier [3]. iPSC neural differentiation medium: DMEM/F12, 2% serum replacement, 1% N2 supplement, 21 mM glutamine, 50 U/mL penicillin/streptomycin, 10 μM SB431542, 2 μM dorsomorphin, and 0.5 μM LDN-193189. Neural progenitor culture medium: DMEM/F12 1:1 Neurobasal, 2% B27 supplement, 2 mM glutamine, 50 U/mL penicillin/streptomycin, 100 ng/mL Shh, 100 ng/mL FGF8, and 2 μM purmorphamine.

Figure 4:
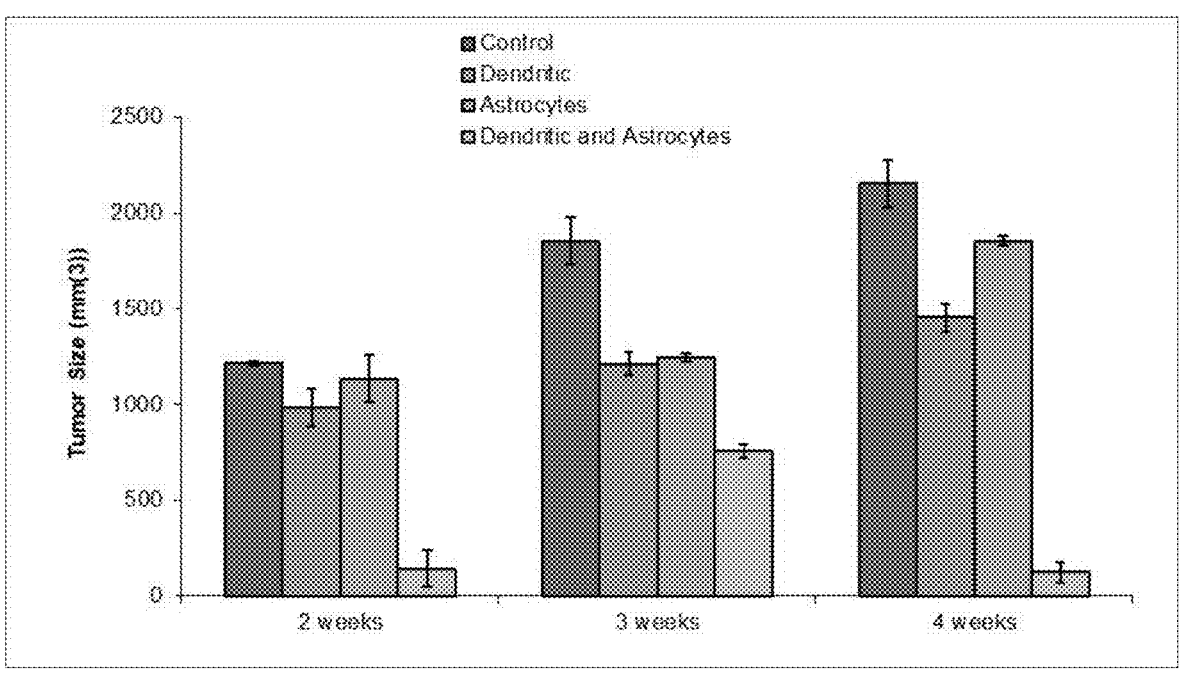
FIG. 4 is a bar graph showing the tumor size of mice based on DCs, Astrocytes, and DCs and Astrocytes

The generated astrocytes were utilized to generate "enhanced" dendritic cells by culture of iPSC derived astrocytes. Human peripheral blood mononuclear cells were cultured with astrocytes at a ratio of 1 to 1 in the presence of IL-4 and GM-CSF at a concentration of 10 ng/ml for 7 days. Cells were pulsed with melanoma B16 lysate and used to immunize C57B/6 mice bearing B16 tumors. One million cancer cell lysates were used for 5 million dendritic cells. Tumors were administered at 1 million cells per mouse. Dendritic cells and astrocytes were administered 5 days after tumor inoculate at half a million cells per mouse. Tumor growth was quantified with calipers and represented below. Results are average of 10 mice per group. Results are shown in FIG. 4.

Figure 5:
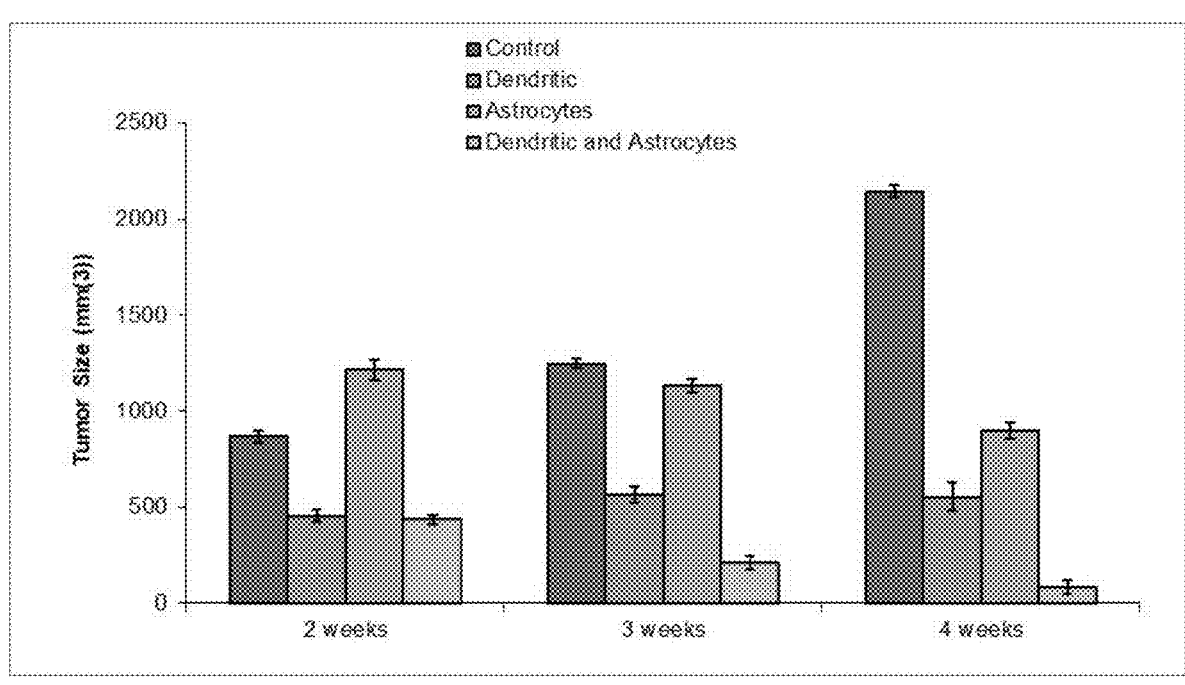
FIG. 5 is a bar graph showing the tumor size of mice based on DCs, Astrocytes, and DCs and Astrocytes

Example 5: Suppression of Lung Cancer Using Astrocyte and Dendritic Cell Immunotherapy Astrocytes and dendritic cells were grown as in example 4. Mice were inoculated with 1 million lewis lung carcinoma cells. Tumors were administered at 1 million cells per mouse. Dendritic cells and astrocytes were administered 5 days after tumor inoculate at half a million cells per mouse. Tumor growth was quantified with calipers and represented below. Results are average of 10 mice per group. Results are shown in FIG. 5.

Figure 6:
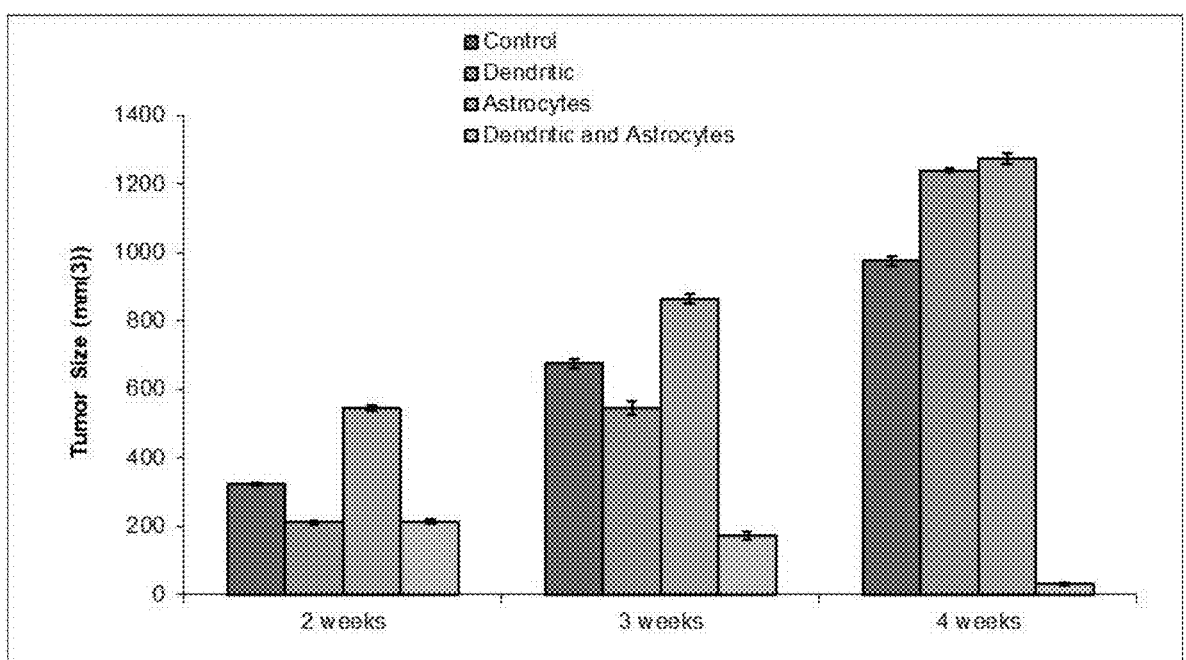
FIG. 6 is a bar graph showing the tumor size of mice based on DCs, Astrocytes, and DCs and Astrocytes

Example 6: Suppression of Glioma Using Astrocyte and Dendritic Cell Immunotherapy Astrocytes and dendritic cells were grown as in example 4. Mice were inoculated with 1 million GL261 cells. Tumors were administered at 1 million cells per mouse. Dendritic cells and astrocytes were administered 5 days after tumor inoculate at half a million cells per mouse. Tumor growth was quantified with calipers and represented below. Results are average of 10 mice per group. Results are shown in FIG. 6.

Figure 7:
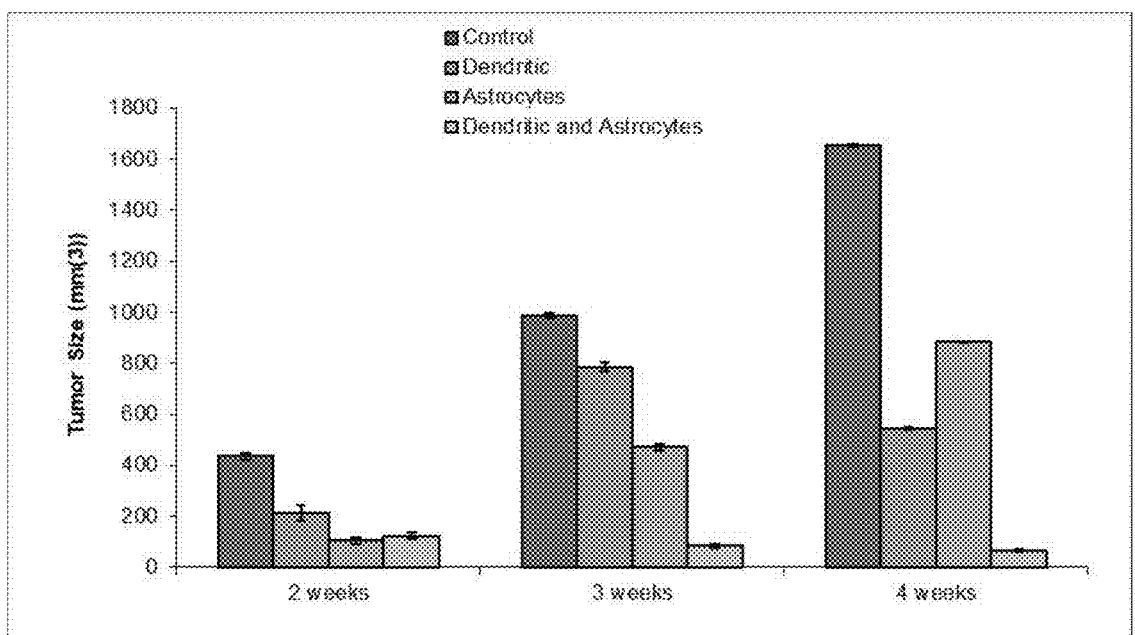
FIG. 7 is a bar graph showing the tumor size of mice based on DCs, Astrocytes, and DCs and Astrocytes

Example 7: Suppression of Colon Cancer Using Astrocyte and Dendritic Cell Immunotherapy Astrocytes and dendritic cells were grown as in example 4. Mice were inoculated with 1 million CT-26 cells. Tumors were administered at 1 million cells per mouse. Dendritic cells and astrocytes were administered 5 days after tumor inoculate at half a million cells per mouse. Tumor growth was quantified with calipers and represented below. Results are average of 10 mice per group. Results are shown in FIG. 7.

Figure 8:
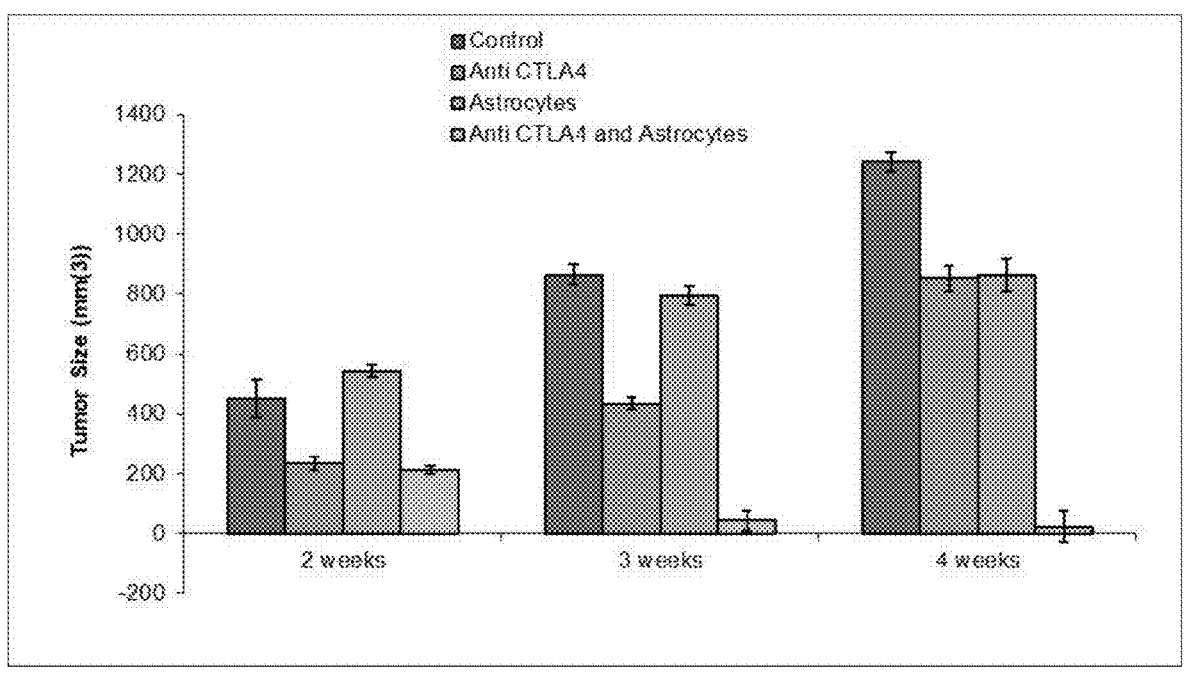
FIG. 8 is a bar graph showing the tumor size of mice based on Anti CTLA4, Astrocytes, and CTLA4 plus Astrocytes

Example 8: Enhanced Efficacy of Checkpoint Inhibitor Anti-CTLA4 by Co-Administration of Astrocytes Astrocytes were grown as in example 4. Mice were inoculated with 1 million B16 cells. Tumors were administered at 1 million cells per mouse. Anti CTLA-4 antibodies (10 ng per mouse) were every second day after tumor administration and astrocytes were administered 5 days after tumor inoculate at half a million cells per mouse. Tumor growth was quantified with calipers and represented below. Results are average of 10 mice per group. Results are shown in FIG. 8.

REFERENCES

1. Nestle, F. O., et al., *Vaccination of melanoma patients with peptide-or tumor lysate-pulsed dendritic cells*. Nat Med, 1998. 4(3): p. 328-32.
2. Chakraborty, N. G., et al., *Immunization with a tumor-cell-lysate-loaded autologous-antigen-presenting-cell-based vaccine in melanoma*. Cancer Immunol Immunother, 1998. 47(1): p. 58-64.
3. Wang, F., et al., *Phase I trial of a MART-1 peptide vaccine with incomplete Freund's adjuvant for resected high-risk melanoma*. Clin Cancer Res, 1999. 5(10): p. 2756-65.
4. Thurner, B., et al., *Vaccination with mage-3A1 peptide pulsed mature, monocyte-derived dendritic cells expands specific cytotoxic T cells and induces regression of some metastases in advanced stage IV melanoma*. J Exp Med, 1999. 190(11): p. 1669-78.
5. Thomas, R., et al., *Immature human monocyte-derived dendritic cells migrate rapidly to draining lymph nodes after intradermal injection for melanoma immunotherapy*. Melanoma Res, 1999. 9(5): p. 474-81.
6. Mackensen, A., et al., *Phase I study in melanoma patients of a vaccine with peptide-pulsed dendritic cells generated in vitro from CD34(+) hematopoietic progenitor cells*. Int J Cancer, 2000. 86(3): p. 385-92.
7. Panelli, M. C., et al., *Phase 1 study in patients with metastatic melanoma of immunization with dendritic cells presenting epitopes derived from the melanoma-associated antigens MART-1 and gp100*. J Immunother, 2000. 23(4): p. 487-98.
8. Schuler-Thurner, B., et al., *Mage-3 and influenza-matrix peptide-specific cytotoxic T cells are inducible in terminal stage HLA-A2.1+ melanoma patients by mature monocyte-derived dendritic cells*. J Immunol, 2000. 165(6): p. 3492-6.
9. Lau, R., et al., *Phase I trial of intravenous peptide pulsed dendritic cells in patients with metastatic melanoma*. J Immunother, 2001. 24(1): p. 66-78.
10. Banchereau, J., et al., *Immune and clinical responses in patients with metastatic melanoma to CD34(+) progenitor-derived dendritic cell vaccine*. Cancer Res, 2001. 61(17): p. 6451-8.
11. Schuler-Thurner, B., et al., *Rapid induction of tumor-specific type 1 T helper cells in metastatic melanoma patients by vaccination with mature, cryopreserved, peptide-loaded monocyte-derived dendritic cells*. J Exp Med, 2002. 195(10): p. 1279-88.
12. Palucka, A. K., et al., *Single injection of CD34+ progenitor-derived dendritic cell vaccine can lead to induction of T-cell immunity in patients with stage IV melanoma*. J Immunother, 2003. 26(5): p. 432-9.
13. Bedrosian, I., et al., *Intranodal administration of peptide pulsed mature dendritic cell vaccines results in superior CD8+T-cell function in melanoma patients*. J Clin Oncol, 2003. 21(20): p. 3826-35.
14. Slingluff, C. L., Jr., et al., *Clinical and immunologic results of a randomized phase II trial of vaccination using four melanoma peptides either administered in granulocyte-macrophage colony-stimulating factor in adjuvant or pulsed on dendritic cells*. J Clin Oncol, 2003. 21(21): p. 4016-26.
15. Hersey, P., et al., *Phase I/II study of treatment with dendritic cell vaccines in patients with disseminated melanoma*. Cancer Immunol Immunother, 2004. 53(2): p. 125-34.
16. Vilella, R., et al., *Pilot study of treatment of biochemo-therapy-refractory stage IV melanoma patients with autologous dendritic cells pulsed with a heterologous melanoma cell line lysate*. Cancer Immunol Immunother, 2004. 53(7): p. 651-8.
17. Palucka, A. K., et al., *Spontaneous proliferation and type 2 cytokine secretion by CD4+T cells in patients with metastatic melanoma vaccinated with antigen-pulsed dendritic cells*. J Clin Immunol, 2005. 25(3): p. 288-95.
18. Banchereau, J., et al., *Immune and clinical outcomes in patients with stage IV melanoma vaccinated with peptide-pulsed dendritic cells derived from CD34+ progenitors and activated with type I interferon*. J Immunother, 2005. 28(5): p. 505-16.
19. Trakatelli, M., et al., *A new dendritic cell vaccine generated with interleukin-3 and interferon-beta induces CD8+ T cell responses against NA17-A2 tumor peptide in melanoma patients*. Cancer Immunol Immunother, 2006. 55(4): p. 469-74.
20. Salcedo, M., et al., *Vaccination of melanoma patients using dendritic cells loaded with an allogeneic tumor cell lysate*. Cancer Immunol Immunother, 2006. 55(7): p. 819-29.
21. Linette, G. P., et al., *Immunization using autologous dendritic cells pulsed with the melanoma-associated antigen gp100-derived G280-9V peptide elicits CD8+ immunity*. Clin Cancer Res, 2005. 11(21): p. 7692-9.
22. Escobar, A., et al., *Dendritic cell immunizations alone or combined with low doses of interleukin-2 induce specific immune responses in melanoma patients*. Clin Exp Immunol, 2005. 142(3): p. 555-68.
23. Tuettenberg, A., et al., *Induction of strong and persistent MelanA/MART-1-specific immune responses by adjuvant dendritic cell-based vaccination of stage II melanoma patients*. Int J Cancer, 2006. 118(10): p. 2617-27.
24. Schadendorf, D., et al., *Dacarbazine (DTIC) versus vaccination with autologous peptide-pulsed dendritic cells (DC) in first-line treatment of patients with metastatic melanoma: a randomized phase III trial of the DC study group of the DeCOG*. Ann Oncol, 2006. 17(4): p. 563-70.
25. Di Pucchio, T., et al., *Immunization of stage IV melanoma patients with Melan-A/MART-1 and gp100 peptides plus IFN-alpha results in the activation of specific CD8(+) T cells and monocyte/dendritic cell precursors*. Cancer Res, 2006. 66(9): p. 4943-51.
26. Nakai, N., et al., *Vaccination of Japanese patients with advanced melanoma with peptide, tumor lysate or both peptide and tumor lysate-pulsed mature, monocyte-derived dendritic cells*. J Dermatol, 2006. 33(7): p. 462-72.

27. Palucka, A. K., et al., *Dendritic cells loaded with killed allogeneic melanoma cells can induce objective clinical responses and MART-1 specific CD8+T-cell immunity*. J Immunother, 2006. 29(5): p. 545-57.
28. Lesimple, T., et al., *Immunologic and clinical effects of injecting mature peptide-loaded dendritic cells by intralymphatic and intranodal routes in metastatic melanoma patients*. Clin Cancer Res, 2006. 12(24): p. 7380-8.
29. Guo, J., et al., *Intratumoral injection of dendritic cells in combination with local hyperthermia induces systemic antitumor effect in patients with advanced melanoma*. Int J Cancer, 2007. 120(11): p. 2418-25.
30. O'Rourke, M. G., et al., *Dendritic cell immunotherapy for stage IV melanoma*. Melanoma Res, 2007. 17(5): p. 316-22.
31. Bercovici, N., et al., *Analysis and characterization of antitumor T-cell response after administration of dendritic cells loaded with allogeneic tumor lysate to metastatic melanoma patients*. J Immunother, 2008. 31(1): p. 101-12.
32. Hersey, P., et al., *Phase I/II study of treatment with matured dendritic cells with or without low dose IL-2 in patients with disseminated melanoma*. Cancer Immunol Immunother, 2008. 57(7): p. 1039-51.
33. von Euw, E. M., et al., *A phase I clinical study of vaccination of melanoma patients with dendritic cells loaded with allogeneic apoptotic/necrotic melanoma cells. Analysis of toxicity and immune response to the vaccine and of IL-10-1082 promoter genotype as predictor of disease progression*. J Transl Med, 2008. 6: p. 6.
34. Carrasco, J., et al., *Vaccination of a melanoma patient with mature dendritic cells pulsed with MAGE-3 peptides triggers the activity of nonvaccine anti-tumor cells*. J Immunol, 2008. 180(5): p. 3585-93.
35. Redman, B. G., et al., *Phase Ib trial assessing autologous, tumor-pulsed dendritic cells as a vaccine administered with or without IL-2 in patients with metastatic melanoma*. J Immunother, 2008. 31(6): p. 591-8.
36. Daud, A. I., et al., *Phenotypic and functional analysis of dendritic cells and clinical outcome in patients with high-risk melanoma treated with adjuvant granulocyte macrophage colony-stimulating factor*. J Clin Oncol, 2008. 26(19): p. 3235-41.
37. Engell-Noerregaard, L., et al., *Review of clinical studies on dendritic cell-based vaccination of patients with malignant melanoma: assessment of correlation between clinical response and vaccine parameters*. Cancer Immunol Immunother, 2009. 58(1): p. 1-14.
38. Nakai, N., et al., Immunohistological *analysis of peptide-induced delayed-type hypersensitivity in advanced melanoma patients treated with melanoma antigen-pulsed mature monocyte-derived dendritic cell vaccination*. J Dermatol Sci, 2009. 53(1): p. 40-7.
39. Dillman, R. O., et al., *Phase II trial of dendritic cells loaded with antigens from self-renewing, proliferating autologous tumor cells as patient-specific antitumor vaccines in patients with metastatic melanoma: final report*. Cancer Biother Radiopharm, 2009. 24(3): p. 311-9.
40. Chang, J. W., et al., *Immunotherapy with dendritic cells pulsed by autologous dactinomycin-induced melanoma apoptotic bodies for patients with malignant melanoma*. Melanoma Res, 2009. 19(5): p. 309-15.
41. Trepiakas, R., et al., *Vaccination with autologous dendritic cells pulsed with multiple tumor antigens for treatment of patients with malignant melanoma: results from a phase I/II trial*. Cytotherapy, 2010. 12(6): p. 721-34.
42. Jacobs, J. F., et al., *Dendritic cell vaccination in combination with anti-CD25 monoclonal antibody treatment. a phase I/II study in metastatic melanoma patients*. Clin Cancer Res, 2010. 16(20): p. 5067-78.
43. Ribas, A., et al., *Multicenter phase II study of matured dendritic cells pulsed with melanoma cell line lysates in patients with advanced melanoma*. J Transl Med, 2010. 8: p. 89.
44. Ridolfi, L., et al., *Unexpected high response rate to traditional therapy after dendritic cell-based vaccine in advanced melanoma: update of clinical outcome and subgroup analysis*. Clin Dev Immunol, 2010. 2010: p. 504979.
45. Cornforth, A. N., et al., *Resistance to the proapoptotic effects of interferon-gamma on melanoma cells used in patient-specific dendritic cell immunotherapy is associated with improved overall survival*. Cancer Immunol Immunother, 2011. 60(1): p. 123-31.
46. Lesterhuis, W. J., et al., *Wild-type and modified gp100 peptide-pulsed dendritic cell vaccination of advanced melanoma patients can lead to long-term clinical responses independent of the peptide used*. Cancer Immunol Immunother, 2011. 60(2): p. 249-60.
47. Bjoern, J., et al., *Changes in peripheral blood level of regulatory T cells in patients with malignant melanoma during treatment with dendritic cell vaccination and low-dose IL-2*. Scand J Immunol, 2011. 73(3): p. 222-33.
48. Steele, J. C., et al., *Phase I/II trial of a dendritic cell vaccine transfected with DNA encoding melan A and gp100 for patients with metastatic melanoma*. Gene Ther, 2011. 18(6): p. 584-93.
49. Kim, D. S., et al., *Immunotherapy of malignant melanoma with tumor lysate-pulsed autologous monocyte-derived dendritic cells*. Yonsei Med J, 2011. 52(6): p. 990-8.
50. Ellebaek, E., et al., *Metastatic melanoma patients treated with dendritic cell vaccination, Interleukin-2 and metronomic cyclophosphamide: results from a phase II trial*. Cancer Immunol Immunother, 2012. 61(10): p. 1791-804.
51. Dillman, R. O., et al., *Tumor stem cell antigens as consolidative active specific immunotherapy: a randomized phase II trial of dendritic cells versus tumor cells in patients with metastatic melanoma*. J Immunother, 2012. 35(8): p. 641-9.
52. Dannull, J., et al., *Melanoma immunotherapy using mature DCs expressing the constitutive proteasome*. J Clin Invest, 2013. 123(7): p. 3135-45.
53. Finkelstein, S. E., et al., *Combination of external beam radiotherapy (EBRT) with intratumoral injection of dendritic cells as neo-adjuvant treatment of high-risk soft tissue sarcoma patients*. Int J Radiat Oncol Biol Phys, 2012. 82(2): p. 924-32.
54. Stift, A., et al., *Dendritic cell vaccination in medullary thyroid carcinoma*. Clin Cancer Res, 2004. 10(9): p. 2944-53.
55. Kuwabara, K., et al., *Results of a phase I clinical study using dendritic cell vaccinations for thyroid cancer*. Thyroid, 2007. 17(1): p. 53-8.
56. Bachleitner-Hofmann, T., et al., *Pilot trial of autologous dendritic cells loaded with tumor lysate(s) from* allogeneic tumor cell lines in patients with metastatic medullary thyroid carcinoma. Oncol Rep, 2009. 21(6): p. 1585-92.

57. Yu, J. S., et al., *Vaccination of malignant glioma patients with peptide pulsed dendritic cells elicits systemic cytotoxicity and intracranial T-cell infiltration.* Cancer Res, 2001. 61(3): p. 842-7.

58. Yamanaka, R., et al., *Vaccination of recurrent glioma patients with tumour lysate-pulsed dendritic cells elicits immune responses: results of a clinical phase I/II trial.* Br J Cancer, 2003. 89(7): p. 1172-9.

59. Yu, J. S., et al., *Vaccination with tumor lysate-pulsed dendritic cells elicits antigen-specific, cytotoxic T-cells in patients with malignant glioma.* Cancer Res, 2004. 64(14): p. 4973-9.

60. Yamanaka, R., et al., *Tumor lysate and IL-18 loaded dendritic cells elicits Th1 response, tumor-specific CD8+ cytotoxic T cells in patients with malignant glioma.* J Neurooncol, 2005. 72(2): p. 107-13.

61. Yamanaka, R., et al., *Clinical evaluation of dendritic cell vaccination for patients with recurrent glioma: results of a clinical phase I/II trial.* Clin Cancer Res, 2005. 11(11): p. 4160-7.

62. Liau, L. M., et al., *Dendritic cell vaccination in glioblastoma patients induces systemic and intracranial T-cell responses modulated by the local central nervous system tumor microenvironment.* Clin Cancer Res, 2005. 11(15): p. 5515-25.

63. Walker, D. G., et al., *Results of a phase I dendritic cell vaccine trial for malignant astrocytoma: potential interaction with adjuvant chemotherapy.* J Clin Neurosci, 2008. 15(2): p. 114-21.

64. Leplina, O. Y., et al., *Use of interferon-alpha-induced dendritic cells in the therapy of patients with malignant brain gliomas.* Bull Exp Biol Med, 2007. 143(4): p. 528-34.

65. De Vleeschouwer, S., et al., *Postoperative adjuvant dendritic cell-based immunotherapy in patients with relapsed glioblastoma multiforme.* Clin Cancer Res, 2008. 14(10): p. 3098-104.

66. Ardon, H., et al., *Adjuvant dendritic cell-based tumour vaccination for children with malignant brain tumours.* Pediatr Blood Cancer, 2010. 54(4): p. 519-25.

67. Prins, R. M., et al., *Gene expression profile correlates with T-cell infiltration and relative survival in glioblastoma patients vaccinated with dendritic cell immunotherapy.* Clin Cancer Res, 2011. 17(6): p. 1603-15.

68. Okada, H., et al., *Induction of CD8+T-cell responses against novel glioma-associated antigen peptides and clinical activity by vaccinations with {alpha}-type 1 polarized dendritic cells and polyinosinic-polycytidylic acid stabilized by lysine and carboxymethylcellulose in patients with recurrent malignant glioma.* J Clin Oncol, 2011. 29(3): p. 330-6.

69. Fadul, C. E., et al., *Immune response in patients with newly diagnosed glioblastoma multiforme treated with intranodal autologous tumor lysate-dendritic cell vaccination after radiation chemotherapy.* J Immunother, 2011. 34(4): p. 382-9.

70. Chang, C. N., et al., *A phase I/II clinical trial investigating the adverse and therapeutic effects of a postoperative autologous dendritic cell tumor vaccine in patients with malignant glioma.* J Clin Neurosci, 2011. 18(8): p. 1048-54.

71. Cho, D. Y., et al., *Adjuvant immunotherapy with whole-cell lysate dendritic cells vaccine for glioblas-* toma multiforme: a phase II clinical trial. World Neurosurg, 2012. 77(5-6): p. 736-44.

72. Iwami, K., et al., *Peptide pulsed dendritic cell vaccination targeting interleukin-13 receptor alpha2 chain in recurrent malignant glioma patients with HLA-A*24/A*02 allele.* Cytotherapy, 2012. 14(6): p. 733-42.

73. Fong, B., et al., *Monitoring of regulatory T cell frequencies and expression of CTLA-4 on T cells, before and after DC vaccination, can predict survival in GBM patients.* PLoS One, 2012. 7(4): p. e32614.

74. De Vleeschouwer, S., et al., *Stratification according to HGG-IMMUNO RPA model predicts outcome in a large group of patients with relapsed malignant glioma treated by adjuvant postoperative dendritic cell vaccination.* Cancer Immunol Immunother, 2012. 61(11): p. 2105-12.

75. Phuphanich, S., et al., *Phase I trial of a multi-epitope-pulsed dendritic cell vaccine for patients with newly diagnosed glioblastoma.* Cancer Immunol Immunother, 2013. 62(1): p. 125-35.

76. Akiyama, Y., et al., *alpha-type-1 polarized dendritic cell-based vaccination in recurrent high-grade glioma: a phase I clinical trial.* BMC Cancer, 2012. 12: p. 623.

77. Prins, R. M., et al., *Comparison of glioma-associated antigen peptide-loaded versus autologous tumor lysate-loaded dendritic cell vaccination in malignant glioma patients.* J Immunother, 2013. 36(2): p. 152-7.

78. Shah, A. H., et al., *Dendritic cell vaccine for recurrent high-grade gliomas in pediatric and adult subjects: clinical trial protocol.* Neurosurgery, 2013. 73(5): p. 863-7.

79. Reichardt, V. L., et al., *Idiotype vaccination using dendritic cells after autologous peripheral blood stem cell transplantation for multiple myeloma—a feasibility study.* Blood, 1999. 93(7): p. 2411-9.

80. Lim, S. H. and R. Bailey-Wood, *Idiotypic protein-pulsed dendritic cell vaccination in multiple myeloma.* Int J Cancer, 1999. 83(2): p. 215-22.

81. Motta, M. R., et al., *Generation of dendritic cells from CD14+ monocytes positively selected by immunomagnetic adsorption for multiple myeloma patients enrolled in a clinical trial of anti-idiotype vaccination.* Br J Haematol, 2003. 121(2): p. 240-50.

82. Reichardt, V. L., et al., *Idiotype vaccination of multiple myeloma patients using monocyte-derived dendritic cells.* Haematologica, 2003. 88(10): p. 1139-49.

83. Guardino, A. E., et al., *Production of myeloid dendritic cells (DC) pulsed with tumor-specific idiotype protein for vaccination of patients with multiple myeloma.* Cytotherapy, 2006. 8(3): p. 277-89.

84. Lacy, M. Q., et al., *Idiotype pulsed antigen presenting cells following autologous transplantation for multiple myeloma may be associated with prolonged survival.* Am J Hematol, 2009. 84(12): p. 799-802.

85. Yi, Q., et al., *Optimizing dendritic cell-based immunotherapy in multiple myeloma: intranodal injections of idiotype-pulsed CD40 ligand-matured vaccines led to induction of type-1 and cytotoxic T-cell immune responses in patients.* Br J Haematol, 2010. 150(5): p. 554-64.

86. Rollig, C., et al., *Induction of cellular immune responses in patients with stage-I multiple myeloma after vaccination with autologous idiotype-pulsed dendritic cells.* J Immunother, 2011. 34(1): p. 100-6.

87. Zahradova, L., et al., *Efficacy and safety of Id-protein-loaded dendritic cell vaccine in patients with multiple myeloma—phase II study results.* Neoplasma, 2012. 59(4): p. 440-9.

88. Timmerman, J. M., et al., *Idiotype pulsed dendritic cell vaccination for B-cell lymphoma: clinical and immune responses in 35 patients.* Blood, 2002. 99(5): p. 1517-26.

89. Maier, T., et al., *Vaccination of patients with cutaneous T-cell lymphoma using intranodal injection of autologous tumor-lysate-pulsed dendritic cells.* Blood, 2003. 102(7): p. 2338-44.

90. Di Nicola, M., et al., *Vaccination with autologous tumor-loaded dendritic cells induces clinical and immunologic responses in indolent B-cell lymphoma patients with relapsed and measurable disease: a pilot study.* Blood, 2009. 113(1): p. 18-27.

91. Hus, I., et al., *Allogeneic dendritic cells pulsed with tumor lysates or apoptotic bodies as immunotherapy for patients with early-stage B-cell chronic lymphocytic leukemia.* Leukemia, 2005. 19(9): p. 1621-7.

92. Li, L., et al., *Immunotherapy for patients with acute myeloid leukemia using autologous dendritic cells generated from leukemic blasts.* Int J Oncol, 2006. 28(4): p. 855-61.

93. Roddie, H., et al., *Phase I/II study of vaccination with dendritic-like leukaemia cells for the immunotherapy of acute myeloid leukaemia.* Br J Haematol, 2006. 133(2): p. 152-7.

94. Litzow, M. R., et al., *Testing the safety of clinical-grade mature autologous myeloid DC in a phase I clinical immunotherapy trial of CML.* Cytotherapy, 2006. 8(3): p. 290-8.

95. Westermann, J., et al., *Vaccination with autologous non-irradiated dendritic cells in patients with bcr/abl+ chronic myeloid leukaemia.* Br J Haematol, 2007. 137(4): p. 297-306.

96. Hus, I., et al., *Vaccination of B-CLL patients with autologous dendritic cells can change the frequency of leukemia antigen-specific CD8+ T cells as well as CD4+CD25+ FoxP3+ regulatory T cells toward an antileukemia response.* Leukemia, 2008. 22(5): p. 1007-17.

97. Palma, M., et al., *Development of a dendritic cell-based vaccine for chronic lymphocytic leukemia.* Cancer Immunol Immunother, 2008. 57(11): p. 1705-10.

98. Van Tendeloo, V. F., et al., *Induction of complete and molecular remissions in acute myeloid leukemia by Wilms' tumor 1 antigen-targeted dendritic cell vaccination.* Proc Natl Acad Sci USA, 2010. 107(31): p. 13824-9.

99. Iwashita, Y., et al., *A phase I study of autologous dendritic cell-based immunotherapy for patients with unresectable primary liver cancer.* Cancer Immunol Immunother, 2003. 52(3): p. 155-61.

100. Lee, W. C., et al., *Vaccination of advanced hepatocellular carcinoma patients with tumor lysate-pulsed dendritic cells: a clinical trial.* J Immunother, 2005. 28(5): p. 496-504.

101. Butterfield, L. H., et al., *A phase I/II trial testing immunization of hepatocellular carcinoma patients with dendritic cells pulsed with four alpha-fetoprotein peptides.* Clin Cancer Res, 2006. 12(9): p. 2817-25.

102. Palmer, D. H., et al., *A phase II study of adoptive immunotherapy using dendritic cells pulsed with tumor lysate in patients with hepatocellular carcinoma.* Hepatology, 2009. 49(1): p. 124-32.

103. El Ansary, M., et al., *Immunotherapy by autologous dendritic cell vaccine in patients with advanced HCC.* J Cancer Res Clin Oncol, 2013. 139(1): p. 39-48.

104. Tada, F., et al., *Phase I/II study of immunotherapy using tumor antigen-pulsed dendritic cells in patients with hepatocellular carcinoma.* Int J Oncol, 2012. 41(5): p. 1601-9.

105. Ueda, Y., et al., *Dendritic cell-based immunotherapy of cancer with carcinoembryonic antigen-derived, HLA-A24-restricted CTL epitope: Clinical outcomes of 18 patients with metastatic gastrointestinal or lung adenocarcinomas.* Int J Oncol, 2004. 24(4): p. 909-17.

106. Hirschowitz, E. A., et al., *Autologous dendritic cell vaccines for non-small-cell lung cancer.* J Clin Oncol, 2004. 22(14): p. 2808-15.

107. Chang, G. C., et al., *A pilot clinical trial of vaccination with dendritic cells pulsed with autologous tumor cells derived from malignant pleural effusion in patients with late-stage lung carcinoma.* Cancer, 2005. 103(4): p. 763-71.

108. Yannelli, J. R., et al., *The large scale generation of dendritic cells for the immunization of patients with non-small cell lung cancer (NSCLC).* Lung Cancer, 2005. 47(3): p. 337-50.

109. Ishikawa, A., et al., *A phase I study of alpha-galactosylceramide (KRN7000)-pulsed dendritic cells in patients with advanced and recurrent non-small cell lung cancer.* Clin Cancer Res, 2005. 11(5): p. 1910-7.

110. Antonia, S. J., et al., *Combination of p53 cancer vaccine with chemotherapy in patients with extensive stage small cell lung cancer.* Clin Cancer Res, 2006. 12(3 Pt 1): p. 878-87.

111. Perrot, I., et al., *Dendritic cells infiltrating human non-small cell lung cancer are blocked at immature stage.* J Immunol, 2007. 178(5): p. 2763-9.

112. Hirschowitz, E. A., et al., *Immunization of NSCLC patients with antigen-pulsed immature autologous dendritic cells.* Lung Cancer, 2007. 57(3): p. 365-72.

113. Baratelli, F., et al., *Pre-clinical characterization of GMP grade CCL21-gene modified dendritic cells for application in a phase I trial in non-small cell lung cancer.* J Transl Med, 2008. 6: p. 38.

114. Hegmans, J. P., et al., *Consolidative dendritic cell-based immunotherapy elicits cytotoxicity against malignant mesothelioma.* Am J Respir Crit Care Med, 2010. 181(12): p. 1383-90.

115. Um, S. J., et al., *Phase I study of autologous dendritic cell tumor vaccine in patients with non-small cell lung cancer.* Lung Cancer, 2010. 70(2): p. 188-94.

116. Chiappori, A. A., et al., *INGN-225: a dendritic cell-based p53 vaccine (Ad.p53-DC) in small cell lung cancer: observed association between immune response and enhanced chemotherapy effect.* Expert Opin Biol Ther, 2010. 10(6): p. 983-91.

117. Perroud, M. W., Jr., et al., *Mature autologous dendritic cell vaccines in advanced non-small cell lung cancer: a phase I pilot study.* J Exp Clin Cancer Res, 2011. 30: p. 65.

118. Skachkova, O. V., et al., *Immunological markers of anti-tumor dendritic cells vaccine efficiency in patients with non-small cell lung cancer.* Exp Oncol, 2013. 35(2): p. 109-13.

119. Hernando, J. J., et al., *Vaccination with autologous tumour antigen-pulsed dendritic cells in advanced gynaecological malignancies: clinical and immunological evaluation of a phase I trial.* Cancer Immunol Immunother, 2002. 51(1): p. 45-52.

120. Rahma, O. E., et al., *A gynecologic oncology group phase II trial of two p53 peptide vaccine approaches: subcutaneous injection and intravenous pulsed dendritic cells in high recurrence risk ovarian cancer patients*. Cancer Immunol Immunother, 2012. 61(3): p. 373-84.

121. Chu, C. S., et al., *Phase I/II randomized trial of dendritic cell vaccination with or without cyclophosphamide for consolidation therapy of advanced ovarian cancer in first or second remission*. Cancer Immunol Immunother, 2012. 61(5): p. 629-41.

122. Kandalaft, L. E., et al., *A Phase I vaccine trial using dendritic cells pulsed with autologous oxidized lysate for recurrent ovarian cancer*. J Transl Med, 2013. 11: p. 149.

123. Lepisto, A. J., et al., *A phase I/II study of a MUC1 peptide pulsed autologous dendritic cell vaccine as adjuvant therapy in patients with resected pancreatic and biliary tumors*. Cancer Ther, 2008. 6(B): p. 955-964.

124. Rong, Y., et al., *A phase I pilot trial of MUC1-peptide-pulsed dendritic cells in the treatment of advanced pancreatic cancer*. Clin Exp Med, 2012. 12(3): p. 173-80.

125. Endo, H., et al., *Phase I trial of preoperative intratumoral injection of immature dendritic cells and OK-432 for resectable pancreatic cancer patients*. J Hepatobiliary Pancreat Sci, 2012. 19(4): p. 465-75.

126. Jackson, L., et al., *Adult mesenchymal stem cells: differentiation potential and therapeutic applications*. J Postgrad Med, 2007. 53(2): p. 121-7.

127. Pittenger, M. F., et al., *Multilineage potential of adult human mesenchymal stem cells*. Science, 1999. 284 (5411): p. 143-7.

128. Banas, A., et al., *Rapid hepatic fate specification of adipose-derived stem cells and their therapeutic potential for liver failure*. J Gastroenterol Hepatol, 2009. 24(1): p. 70-7.

129. Lee, K. D., et al., *In vitro hepatic differentiation of human mesenchymal stem cells*. Hepatology, 2004. 40(6): p. 1275-84.

130. Cho, K. A., et al., *Mesenchymal stem cells showed the highest potential for the regeneration of injured liver tissue compared with other subpopulations of the bone marrow*. Cell Biol Int, 2009. 33(7): p. 772-7.

131. Hong, S. H., et al., *In vitro differentiation of human umbilical cord blood-derived mesenchymal stem cells into hepatocyte-like cells*. Biochem Biophys Res Commun, 2005. 330(4): p. 1153-61.

132. Ishikawa, T., et al., *Stem cells for hepatic regeneration: the role of adipose tissue derived mesenchymal stem cells*. Curr Stem Cell Res Ther, 2010. 5(2): p. 182-9.

133. Seo, M. J., et al., *Differentiation of human adipose stromal cells into hepatic lineage in vitro and in vivo*. Biochem Biophys Res Commun, 2005. 328(1): p. 258-64.

134. Crisan, M., et al., *A perivascular origin for mesenchymal stem cells in multiple human organs*. Cell Stem Cell, 2008. 3(3): p. 301-13.

135. Tavian, M. and B. Peault, *Embryonic development of the human hematopoietic system*. Int J Dev Biol, 2005. 49(2-3): p. 243-50.

136. Peault, B., et al., *Stem and progenitor cells in skeletal muscle development, maintenance, and therapy*. Mol Ther, 2007. 15(5): p. 867-77.

137. Aggarwal, S. and M. F. Pittenger, *Human mesenchymal stem cells modulate allogeneic immune cell responses*. Blood, 2005. 105(4): p. 1815-22.

138. Caplan, A. I., *Adult mesenchymal stem cells for tissue engineering versus regenerative medicine*. J Cell Physiol, 2007. 213(2): p. 341-7.

139. Chamberlain, G., et al., *Concise review: mesenchymal stem cells: their phenotype, differentiation capacity, immunological features, and potential for homing*. Stem Cells, 2007. 25(11): p. 2739-49.

140. Banas, A., et al., *IFATS collection: in vivo therapeutic potential of human adipose tissue mesenchymal stem cells after transplantation into mice with liver injury*. Stem Cells, 2008. 26(10): p. 2705-12.

141. Kharaziha, P., et al., *Improvement of liver function in liver cirrhosis patients after autologous mesenchymal stem cell injection: a phase I-II clinical trial*. Eur J Gastroenterol Hepatol, 2009. 21(10): p. 1199-205.

142. Kuo, T. K., et al., *Stem cell therapy for liver disease: parameters governing the success of using bone marrow mesenchymal stem cells*. Gastroenterology, 2008. 134(7): p. 2111-21, 2121 el-3.

143. Chang, Y. J., et al., *Mesenchymal stem cells facilitate recovery from chemically induced liver damage and decrease liver fibrosis*. Life Sci, 2009. 85(13-14): p. 517-25.

144. Lu, L. L., et al., *Isolation and characterization of human umbilical cord mesenchymal stem cells with hematopoiesis-supportive function and other potentials*. Haematologica, 2006. 91(8): p. 1017-26.

145. Mohamadnejad, M., et al., *Phase 1 trial of autologous bone marrow mesenchymal stem cell transplantation in patients with decompensated liver cirrhosis*. Arch Iran Med, 2007. 10(4): p. 459-66.

146. Terai, S., et al., *Improved liver function in patients with liver cirrhosis after autologous bone marrow cell infusion therapy*. Stem Cells, 2006. 24(10): p. 2292-8.

147. Chang, C. J., et al., *Placenta-derived multipotent cells exhibit immunosuppressive properties that are enhanced in the presence of interferon-gamma*. Stem Cells, 2006. 24(11): p. 2466-77.

148. Iyer, S. S. and M. Rojas, *Anti-inflammatory effects of mesenchymal stem cells: novel concept for future therapies*. Expert Opin Biol Ther, 2008. 8(5): p. 569-81.

149. Nauta, A. J. and W. E. Fibbe, *Immunomodulatory properties of mesenchymal stromal cells*. Blood, 2007. 110(10): p. 3499-506.

150. Uccelli, A., V. Pistoia, and L. Moretta, *Mesenchymal stem cells: a new strategy for immunosuppression?* Trends Immunol, 2007. 28(5): p. 219-26.

151. Wolbank, S., et al., *Dose-dependent immunomodulatory effect of human stem cells from amniotic membrane: a comparison with human mesenchymal stem cells from adipose tissue*. Tissue Eng, 2007. 13(6): p. 1173-83.

152. Wolf, D. and A. M. Wolf, *Mesenchymal stem cells as cellular immunosuppressants*. Lancet, 2008. 371 (9624): p. 1553-4.

153. Shi, M., Z. W. Liu, and F. S. Wang, *Immunomodulatory properties and therapeutic application of mesenchymal stem cells*. Clin Exp Immunol, 2011. 164(1): p. 1-8.

154. Sordi, V. and L. Piemonti, *Therapeutic plasticity of stem cells and allograft tolerance*. Cytotherapy, 2011. 13(6): p. 647-60.

155. Popp, F. C., et al., *Mesenchymal stem cells as immunomodulators after liver transplantation.* Liver Transpl, 2009. 15(10): p. 1192-8.

156. Friedenstein, A. J., R. K. Chailakhjan, and K. S. Lalykina, *The development of fibroblast colonies in monolayer cultures of guinea-pig bone marrow and spleen cells.* Cell Tissue Kinet, 1970. 3(4): p. 393-403.

157. Friedenstein, A. J., et al., *Stromal cells responsible for transferring the microenvironment of the hemopoietic tissues. Cloning in vitro and retransplantation in vivo.* Transplantation, 1974. 17(4): p. 331-40.

158. Caplan, A. I., *Molecular and cellular differentiation of muscle, cartilage, and bone in the developing limb.* Prog Clin Biol Res, 1986. 217B: p. 307-18.

159. Caplan, A. I., *Mesenchymal stem cells.* J Orthop Res, 1991. 9(5): p. 641-50.

160. Kopen, G. C., D. J. Prockop, and D. G. Phinney, *Marrow stromal cells migrate throughout forebrain and cerebellum, and they differentiate into astrocytes after injection into neonatal mouse brains.* Proc Natl Acad Sci USA, 1999. 96(19): p. 10711-6.

161. Petersen, B. E., et al., *Bone marrow as a potential source of hepatic oval cells.* Science, 1999. 284(5417): p. 1168-70.

162. Teratani, T., et al., *Direct hepatic fate specification from mouse embryonic stem cells.* Hepatology, 2005. 41(4): p. 836-46.

163. Le Blanc, K. and O. Ringden, *Immunomodulation by mesenchymal stem cells and clinical experience.* J Intern Med, 2007. 262(5): p. 509-25.

164. Keyser, K. A., K. E. Beagles, and H. P. Kiem, *Comparison of mesenchymal stem cells from different tissues to suppress T-cell activation.* Cell Transplant, 2007. 16(5): p. 555-62.

165. Le Blanc, K., et al., *Mesenchymal stem cells for treatment of steroid-resistant, severe, acute graft-versus-host disease: a phase II study.* Lancet, 2008. 371 (9624): p. 1579-86.

166. Ning, H., et al., *The correlation between cotransplantation of mesenchymal stem cells and higher recurrence rate in hematologic malignancy patients: outcome of a pilot clinical study.* Leukemia, 2008. 22(3): p. 593-9.

167. Ball, L., et al., *Third party mesenchymal stromal cell infusions fail to induce tissue repair despite successful control of severe grade IV acute graft-versus-host disease in a child with juvenile myelo-monocytic leukemia.* Leukemia, 2008. 22(6): p. 1256-7.

168. Ringden, O., et al., *Mesenchymal stem cells for treatment of therapy-resistant graft-versus-host disease.* Transplantation, 2006. 81(10): p. 1390-7.

169. Le Blanc, K., et al., *Treatment of severe acute graft-versus-host disease with third party haploidentical mesenchymal stem cells.* Lancet, 2004. 363(9419): p. 1439-41.

170. Muller, I., et al., *Application of multipotent mesenchymal stromal cells in pediatric patients following allogeneic stem cell transplantation.* Blood Cells Mol Dis, 2008. 40(1): p. 25-32.

171. Horwitz, E. M., et al., *Isolated allogeneic bone marrow-derived mesenchymal cells engraft and stimulate growth in children with osteogenesis imperfecta: Implications for cell therapy of bone.* Proc Natl Acad Sci USA, 2002. 99(13): p. 8932-7.

172. Koc, O. N., et al., Allogeneic *mesenchymal stem cell infusion for treatment of metachromatic leukodystrophy (MLD) and Hurler syndrome (MPS-IH).* Bone Marrow Transplant, 2002. 30(4): p. 215-22.

173. Le Blanc, K., et al., *Transplantation of mesenchymal stem cells to enhance engraftment of hematopoietic stem cells.* Leukemia, 2007. 21(8): p. 1733-8.

174. Lazarus, H. M., et al., *Cotransplantation of HLA-identical sibling culture-expanded mesenchymal stem cells and hematopoietic stem cells in hematologic malignancy patients.* Biol Blood Marrow Transplant, 2005. 11(5): p. 389-98.

175. Ball, L. M., et al., *Cotransplantation of ex vivo expanded mesenchymal stem cells accelerates lymphocyte recovery and may reduce the risk of graft failure in haploidentical hematopoietic stem-cell transplantation.* Blood, 2007. 110(7): p. 2764-7.

176. http://www.osiristx.com/pdf/PR%2039%2025Mar07%20Provacel%20Positive %20Results.pdf.

177. Kurtzberg, J., et al., *Allogeneic human mesenchymal stem cell therapy (remestemcel-L, Prochymal) as a rescue agent for severe refractory acute graft-versus-host disease in pediatric patients.* Biol Blood Marrow Transplant, 2014. 20(2): p. 229-35.

178. Kellathur, S. N. and H. X. Lou, *Cell and tissue therapy regulation: worldwide status and harmonization.* Biologicals, 2012. 40(3): p. 222-4.

The invention claimed is:

1. A method of treatment cancer comprising the steps of: a) obtaining a population of astrocyte cells; b) contacting said population of astrocyte cells with a population of dendritic cells; c) introducing one or more tumor antigens into said culture of astrocyte cells with dendritic cells; d) inducing maturation of said dendritic cells and e) administering said activated dendritic cells into a mammal in need of treatment.

2. The method of claim 1, wherein said astrocyte cells are derived from mammalian astrocyte progenitor cells being CD44 immunoreactive.

3. The method of claim 2, wherein said astrocyte progenitor cells express CD105.

4. The method of claim 2, wherein said astrocyte progenitor cells express CD123.

5. The method of claim 2, wherein said astrocyte progenitor cells express IL-3 receptor.

6. The method of claim 2, wherein said astrocyte progenitor cells express c-met.

7. The method of claim 2, wherein said astrocyte progenitor cells express Nanog.

8. The method of claim 2, wherein said astrocyte progenitor cells express Sox-2.

9. The method of claim 2, wherein said astrocyte progenitor cells express aldehyde dehydrogenase family 1 member L1 (Aldh1L1).

10. The method of claim 2, wherein said astrocyte progenitor cells express aldolase C (AldoC).

11. The method of claim 2, wherein said astrocyte progenitor cells glutamate transporter-1 (Glt1).

12. The method of claim 2, wherein said astrocyte progenitor cells express S100 calcium-binding protein B (S100b).

13. The method of claim 2, wherein said astrocyte progenitor cells express Aquaporin 4.

* * * * *